United States Patent
Sato et al.

(10) Patent No.: US 7,144,373 B2
(45) Date of Patent: Dec. 5, 2006

(54) APPARATUS AND METHOD FOR DETECTING PULSE WAVE

(75) Inventors: Hironori Sato, Moriyama (JP); Tomoki Kitawaki, Okayama (JP); Masao Hashimoto, Kyoto (JP)

(73) Assignee: Omron Healthcare Co., Ltd., Kyoto (JP)

(*) Notice: Subject to any disclaimer, the term of this patent is extended or adjusted under 35 U.S.C. 154(b) by 555 days.

(21) Appl. No.: 10/753,076

(22) Filed: Jan. 8, 2004

(65) Prior Publication Data

US 2004/0193061 A1    Sep. 30, 2004

(30) Foreign Application Priority Data

Jan. 21, 2003   (JP) .............................. 2003-012313

(51) Int. Cl.
*A61B 5/00*   (2006.01)
(52) U.S. Cl. ...................... 600/490; 600/485; 600/500; 600/501
(58) Field of Classification Search ................ 600/491, 600/501, 500, 502, 485
See application file for complete search history.

(56) References Cited

U.S. PATENT DOCUMENTS 5,238,000 A * 8/1993 Niwa .......................... 600/502
5,467,771 A * 11/1995 Narimatsu et al. ........... 600/485
6,228,034 B1 * 5/2001 Voss et al. .................... 600/485
6,491,467 B1 * 12/2002 Mitsuya ........................ 401/195
7,048,691 B1 * 5/2006 Miele et al. .................. 600/504

FOREIGN PATENT DOCUMENTS

JP            01-285244       11/1989
JP            06-090912       4/1994

* cited by examiner

*Primary Examiner*—Charles A. Marmor, II
*Assistant Examiner*—Karen E. Toth
(74) *Attorney, Agent, or Firm*—Morrison & Foerster LLP

(57) ABSTRACT

Provided are an apparatus and method of detecting a pulse wave at the certain position of an artery. A pressure sensor array has a pressurization surface on which plural pressure sensors are disposed in a direction intersecting with an artery. The pressurization surface, when a pulse wave is detected, is pressed against a surface of a living human body by a cuff pressure in a pressurization cuff. CPU, when a pulse wave is detected, inputs voltage signals indicating pressure information from the plural pressure sensors simultaneously along with the time axis. CPU extracts the DC component indicating a pressure component caused by a hard member from a voltage signal to specify the pressure sensor located above the hard member from the extracted DC component. The pressure sensors left after the specified pressure sensor located above the hard member among the plural pressure sensors are selected as candidates of the pressure sensor located above the artery to detect a pulse wave generated in the artery based on pressure information outputted from the selected pressure sensors.

19 Claims, 18 Drawing Sheets

Fig. 12
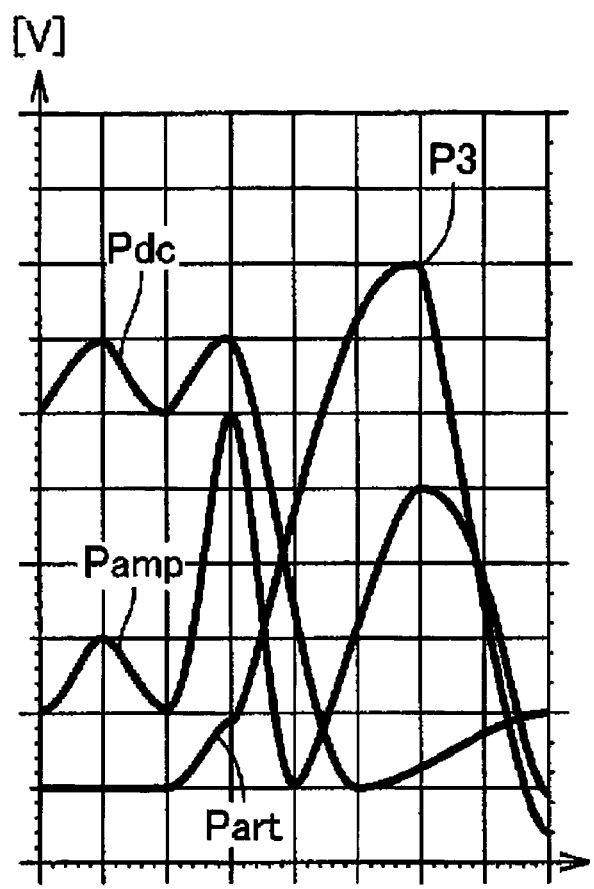
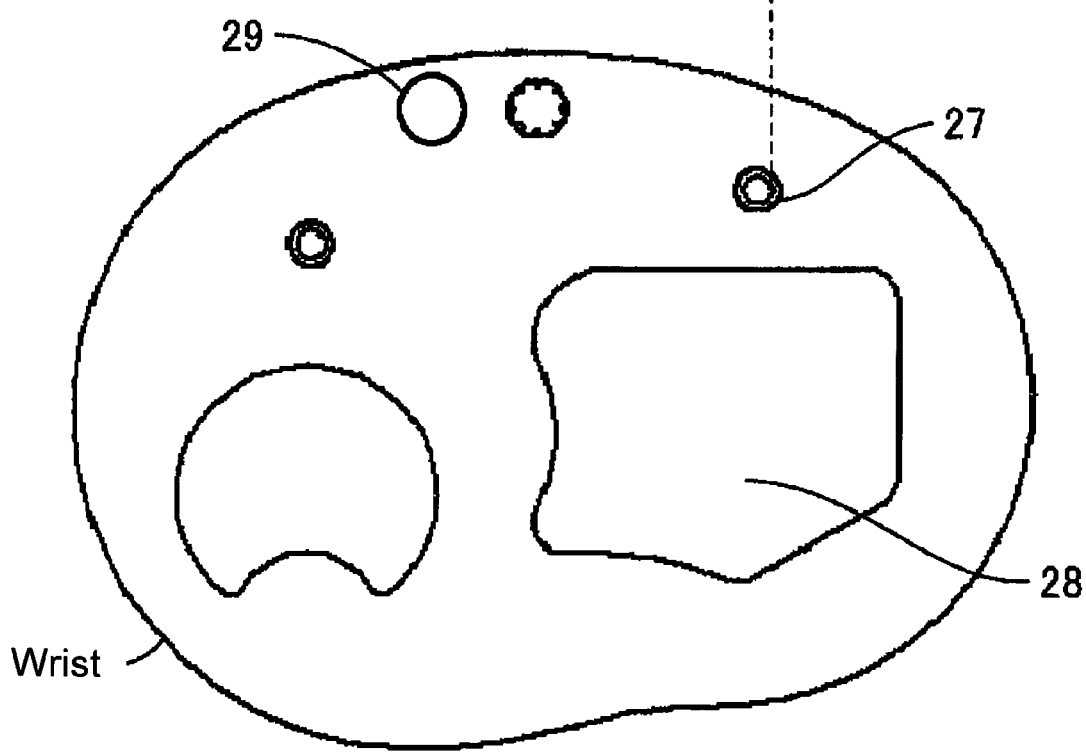
Wrist

Fig. 13
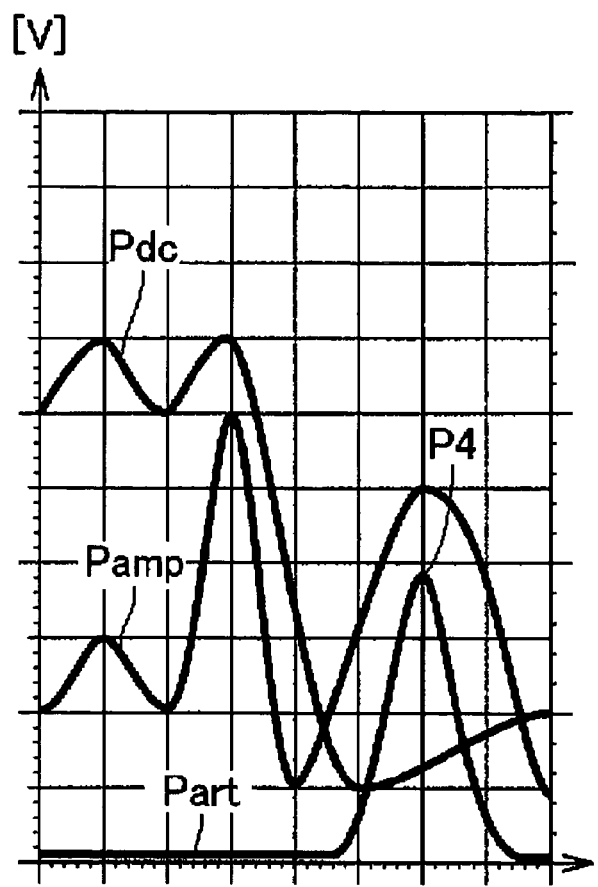
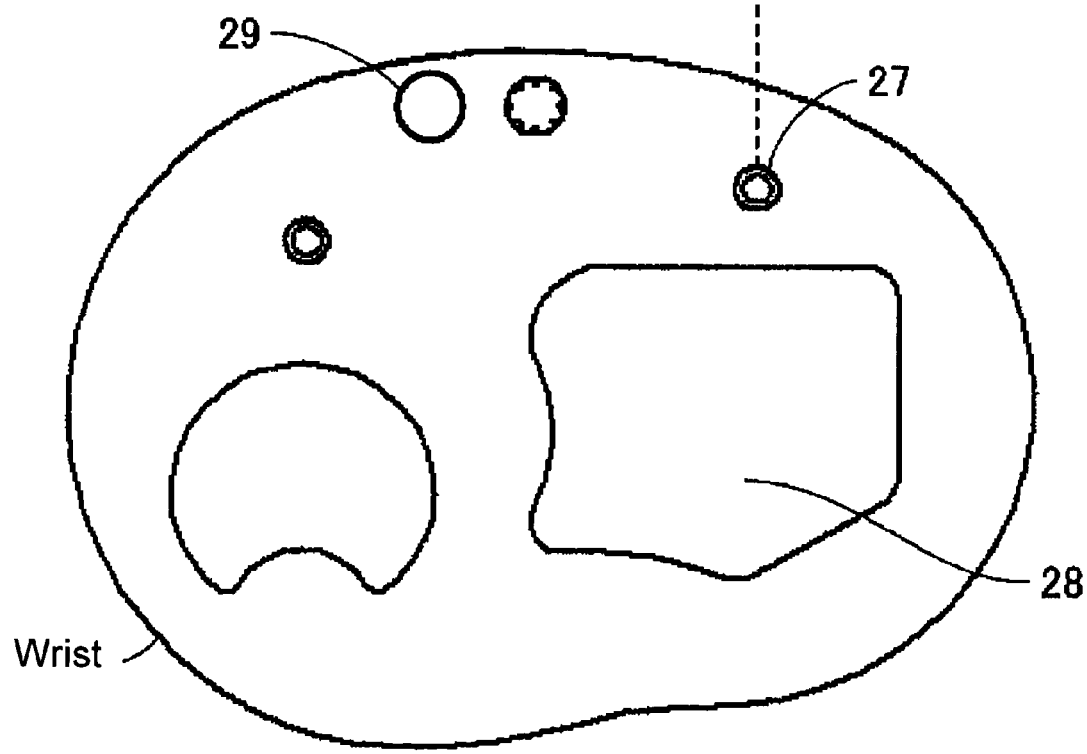

APPARATUS AND METHOD FOR DETECTING PULSE WAVE

BACKGROUND OF THE INVENTION

1. Field of the Invention

The present invention relates to an apparatus and method of detecting a pulse wave, and particularly, to an apparatus and method searching a proper artery position to detect a pulse wave at the searched artery position.

2. Description of the Related Art

A pulse wave is detected based on pressure information that is a voltage signal obtained from an pressure detecting element pressed against a human body surface above an artery. The pressure information shows a pulse pressure, the pulse pressure originates from a change in arterial volume caused by pressurization and a waveform showing the change is acquired as a pulse wave. As pulse wave detecting apparatuses, there have been available an apparatus determining whether or not a pressurization position is proper based on whether or not an amplitude of a pulse wave when a pressurization force reaches a predetermined level is a predetermined value or less (for example, see patent document 1, which are the specification and drawings of Japanese Unexamined Patent Publication No. 01-285244) and an apparatus having a function determining whether or not a pressurization state of a pressure detecting element is proper (for example, see patent document 2, which is the specification and drawings of Japanese Unexamined Patent Publication No. 06-90912).

Since the prior art pulse wave detecting apparatuses, however, have no function specifying positions of hard members such as a bone and a tendon at a pressurization site and therefore, have difficulty detecting a pulse wave at a proper artery position, a detected pulse wave includes an artifact pulse wave, which causes a high detection precision to be obtained with difficulty. The term "artifact pule wave" means an AC noise component in a voltage signal caused by a hard member.

SUMMARY OF THE INVENTION

It is accordingly an object of the invention to provide an apparatus and method capable of detecting a pulse wave at an artery position.

A pulse wave detecting apparatus according an aspect of the invention is directed to a pulse wave detecting apparatus including: a pressure sensor array that has a surface on which plural pressure sensors are disposed, the surface being pressed against an artery of a living human body so that a disposing direction of the pressure sensors intersects with the artery; an pressurization section pressing the surface of the pressure sensor array against the artery; a sensor selecting section selecting a candidate of the pressure sensor located above the artery from the pressure sensors in the pressure sensor array pressed by the pressurization section; and a pulse wave detecting section detecting a pulse wave generated in the artery based on pressure information outputted from the pressure sensor selected by the sensor selecting section in the course where a pressurization force imposed on the pressure sensor array is continuously changed by the pressurization section.

The sensor selecting section includes: a pressure information acquiring section acquiring pressure information from the respective pressure sensors of the pressure sensor array simultaneously along the time axis; and a hard member sensor excluding section.

The hard member sensor excluding section extracts information on a pressure component caused by a hard member of a living human body different from an artery thereof, from pressure information of the respective pressure sensors acquired by the pressure information acquiring section, specifies the pressure sensor located above a hard member from the extracted pressure component information and selects the pressure sensors left after the specified pressure sensor is excluded from the plural pressure sensors as candidates of the pressure sensor located above the artery.

With the pulse wave detecting apparatus, the pressure sensors left after the pressure sensor located above a hard member specified by the hard member excluding section is excluded from the plural pressure sensors using pressure component information are selected as candidates of the pressure sensor located above the artery to detect a pulse wave generated from the artery based on pressure information outputted from the selected pressure sensors.

Accordingly, a pulse wave can be detected at the position of an artery but not at the position of a hard member which differs from the artery.

In the pulse wave detecting apparatus, it is preferable that pressure information is a voltage signal, pressure component information is the DC component of the voltage signal and the hard member sensor excluding section extracts the DC component from the voltage signal to specify the pressure sensor located above a hard member based on a level of the extracted DC component.

Therefore, it is possible to specify the pressure sensor detecting a pressure caused by a hard member based on DC components of voltage signals of the pressure sensors, that is the pressure sensor located above the hard member.

The hard member sensor excluding section preferably specifies that the pressure sensor having a DC component at a level exceeding a predetermined level is a pressure sensor with a high possibility of being located above a hard member.

Accordingly, it is possible to specify the pressure sensor with a high possibility of being located above a hard member, that is the pressure sensor located at a position other than above an artery, based on the fact that a level of the DC component of a voltage signal outputted from the pressure sensor exceeds a predetermined level.

The hard member sensor excluding section preferably specifies that the pressure sensor with a DC component at the highest level among the plural pressure sensors is located above a hard member.

Therefore, it is possible to specify the pressure sensor located above a hard member among the plural pressure sensors based on the fact that the DC component of the voltage signal outputted from the pressure sensor is at the highest level.

The hard member sensor excluding section preferably specifies the pressure sensor located above a hard member based on an inclination of a slope of a waveform obtained by connecting DC component levels of the plural pressure sensors in a disposing direction thereof.

Accordingly, a direction in which a position of a hard member is located can be determined based on amounts of changes in DC components in the disposing direction, thereby enabling a pressure sensor located in the determined direction to be specified as the pressure sensor located above a hard member.

The sensor selecting section preferably further includes an artery position information generating section generating artery position information for selecting the pressure sensor located above an artery from pulse wave amplitude information and pressure component information included in pressure information of the respective pressure sensors acquired by the pressure information acquiring section.

Therefore, the artery position information generating section can select the pressure sensor located above an artery based on artery position information generated from pulse wave amplitude information and pressure component information included in pressure information of the respective sensors.

In the pulse wave detecting apparatus, it is preferable that pulse wave amplitude information is the AC component of a voltage signal, the AC component includes a pulse wave component and an artifact pulse wave, and the artery position information generating section includes an artifact removing section acquiring a pulse wave component left after the artifact pulse wave is removed from the AC component as artery position information.

Accordingly, the artery position information for selecting the pressure sensor located on the artery can be acquired as a pulse wave component left after the artifact pulse wave is removed from the AC component by the artifact removing section.

The artifact removing section preferably removes the artifact pulse wave from the AC component using the DC component.

Therefore, the artery position information can be acquired by removing the artifact pulse wave from the AC component using the DC component.

The artifact removing section preferably removes the artifact pulse wave from the AC component by normalizing the AC component through division of the AC component by the DC component. Therefore, the artery position information can be obtained by normalizing the AC component through division of the AC component by the DC component.

The artifact removing section preferably removes the artifact pulse wave from the AC component by subtracting the DC component from the AC component. Therefore, the artery position information can be obtained by subtracting the DC component from the AC component.

The pulse wave detecting apparatus preferably further includes a hard member position notifying section notifying the position of a hard member relative to a pressure sensor array based on a position in the disposition of the pressure sensor specified as being located above a hard member by the hard member sensor excluding section.

Therefore, a position of a hard member in a living human body relative to a sensor array can be notified when a pulse wave is detected.

The pulse wave detecting apparatus preferably further includes an artery position notifying section notifying a position of an artery relative to a pressure sensor array based on the position in the disposition of a candidate of the pressure sensor selected as being located above the artery by the sensor selecting section.

Therefore, the position of an artery in a living human body relative to a pressure sensor array can be notified when a pulse wave is detected.

It is preferable that the pulse wave detecting apparatus, in which a pressure sensor array can be moved by sliding in a disposing direction thereof, further includes a notification section notifying a sliding direction of the pressure sensor array for detecting a pule wave based on a position in the disposition of the pressure sensor specified as being located above a hard member by the hard member sensor excluding section.

Accordingly, a sliding direction of a pressure sensor array for detecting a pulse wave can be notified based on the position of a hard member in a living human body.

It is preferable that the pulse wave detecting apparatus, in which a pressure sensor array can be moved by sliding in a disposing direction thereof, further includes a notification section notifying a sliding direction of a pressure sensor array for detecting a pulse wave based on a position in the disposition of a candidate of the pressure sensor selected as being located above an artery by the sensor selecting section.

Therefore, a sliding direction of a pressure sensor array for detecting a pulse wave can be notified based on the position of an artery in a living human body.

It is preferable that the pulse wave detecting apparatus, in which a pressure sensor array can be moved by sliding in a disposing direction thereof, further includes a notification section notifying a sliding direction of a pressure sensor array for detecting a pulse wave based on a position in the disposition of the pressure sensor specified as being located above a hard member by the hard member sensor excluding section and a position in the disposition of a candidate of the pressure sensor selected as being located above an artery by the sensor selecting section.

Accordingly, a sliding direction of a pressure sensor array for detecting a pulse wave can be notified based on the position of a hard member and the position of an artery in a living human body.

The notification is preferably effected using light emitting units provided being related to a pressure sensor array.

According to another aspect of the invention, a method of detecting a pulse wave is a method detecting a pulse wave generated in an artery of a living human body based on pressure information outputted from a pressure sensor in the course where a pressurization force imposed on a pressure sensor array, which has a surface on which plural pressure sensors are disposed, the surface being disposed above the artery of the living human body and being pressed against the artery thereof so that a disposing direction of the pressure sensors intersects with the artery, is continuously changed, including a sensor selecting step selecting a candidate of the pressure sensor located above the artery among the pressure sensors of the pressure sensor array.

The sensor selecting step includes: a pressure information acquiring step of acquiring pressure information from the respective pressure sensors of the pressure sensor array simultaneously along the time axis; and a hard member sensor excluding step. In the hard member sensor excluding step, information on a pressure component caused by a hard member of a living human body different from an artery thereof is extracted from pressure information outputted by the respective pressure sensors acquired in the pressure information acquiring step, the pressure sensor located above a hard member is specified from the extracted pressure component information and the pressure sensors left after the specified pressure sensor is excluded among the plural pressure sensors is selected as candidates of the pressure sensor located above the artery.

According to the pulse wave detecting method, the pressure sensors left after the pressure sensor located above a hard member specified in the hard member sensor excluding step using pressure component information is excluded among the plural pressure sensors are selected as candidates of the pressure sensor located above an artery and a pulse wave generated in the artery is detected based on pressure information outputted from the selected pressure sensor.

Therefore, a pulse wave can be detected at the position of an artery but not at the position of a hard member different from the artery.

BRIEF DESCRIPTION OF THE DRAWINGS

FIG. 12 shows a graph of an example of a procedure in processing specifying a sensor as an optimal channel from output characteristics of a pressure sensor array relating to an embodiment of the invention.

FIG. 13 shows a representation of another example of a procedure in processing specifying a sensor as an optimal channel from output characteristics of a pressure sensor array relating to an embodiment of the invention.

DESCRIPTION OF THE PREFERRED EMBODIMENTS

Detailed description will be given of embodiments of the invention below with reference to the accompanying drawings.

Figure 1:
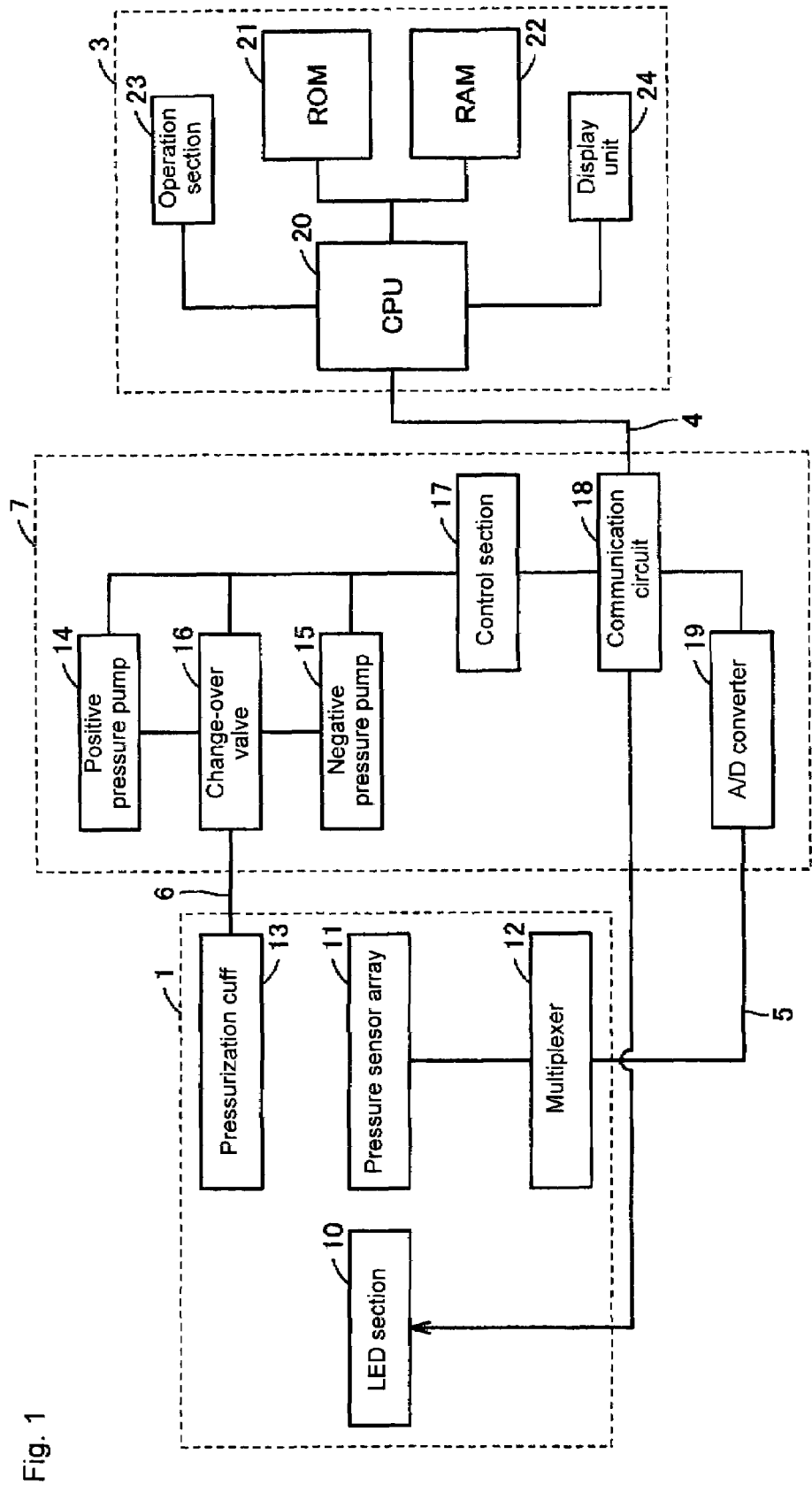
FIG. 1 shows a functional architecture of a pulse wave detecting apparatus relating to an embodiment of the invention.
Figure 2:
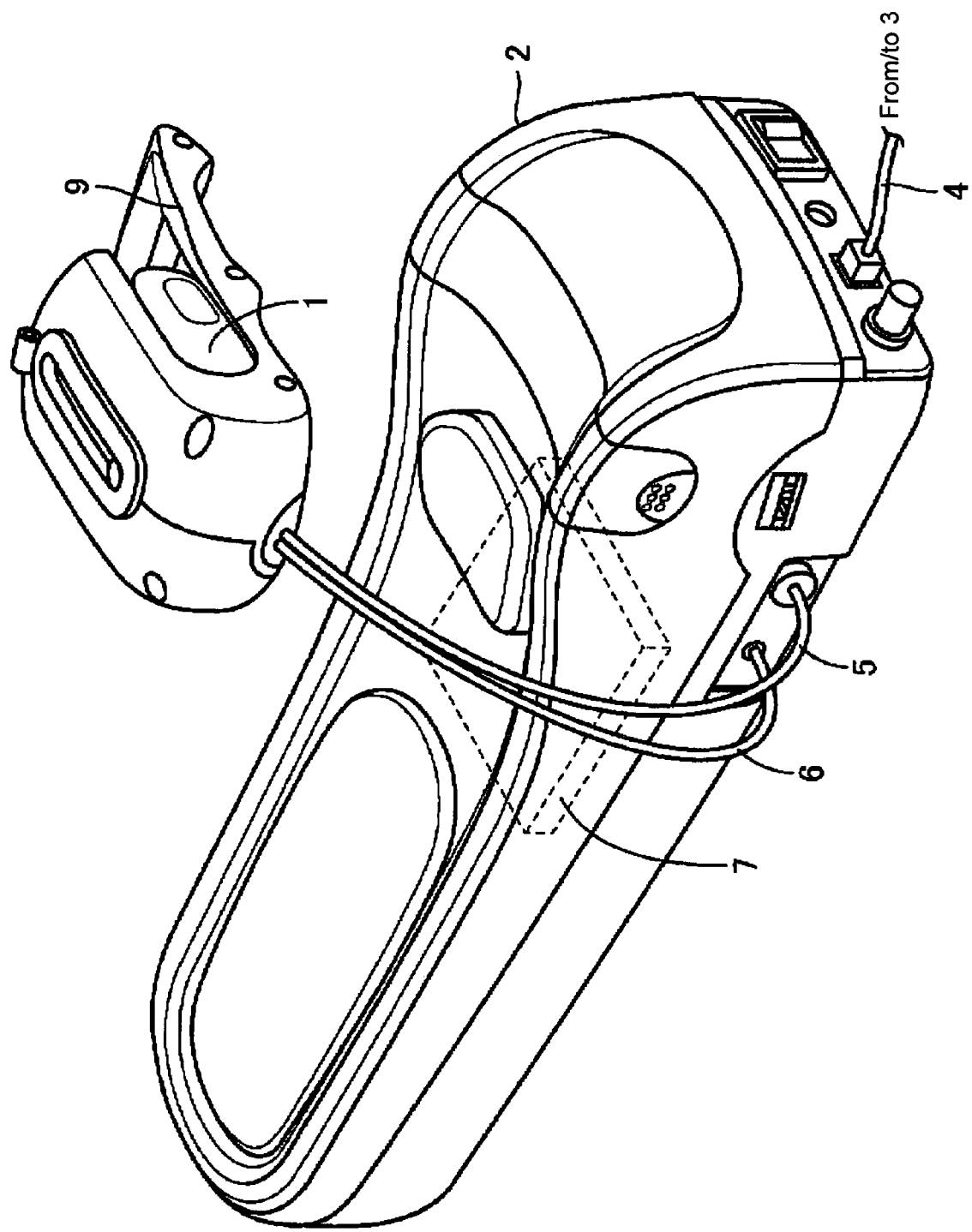
FIG. 2 shows a view of a way of connection between a sensor unit and a fixing stand relating to an embodiment of the invention.
Figure 3:
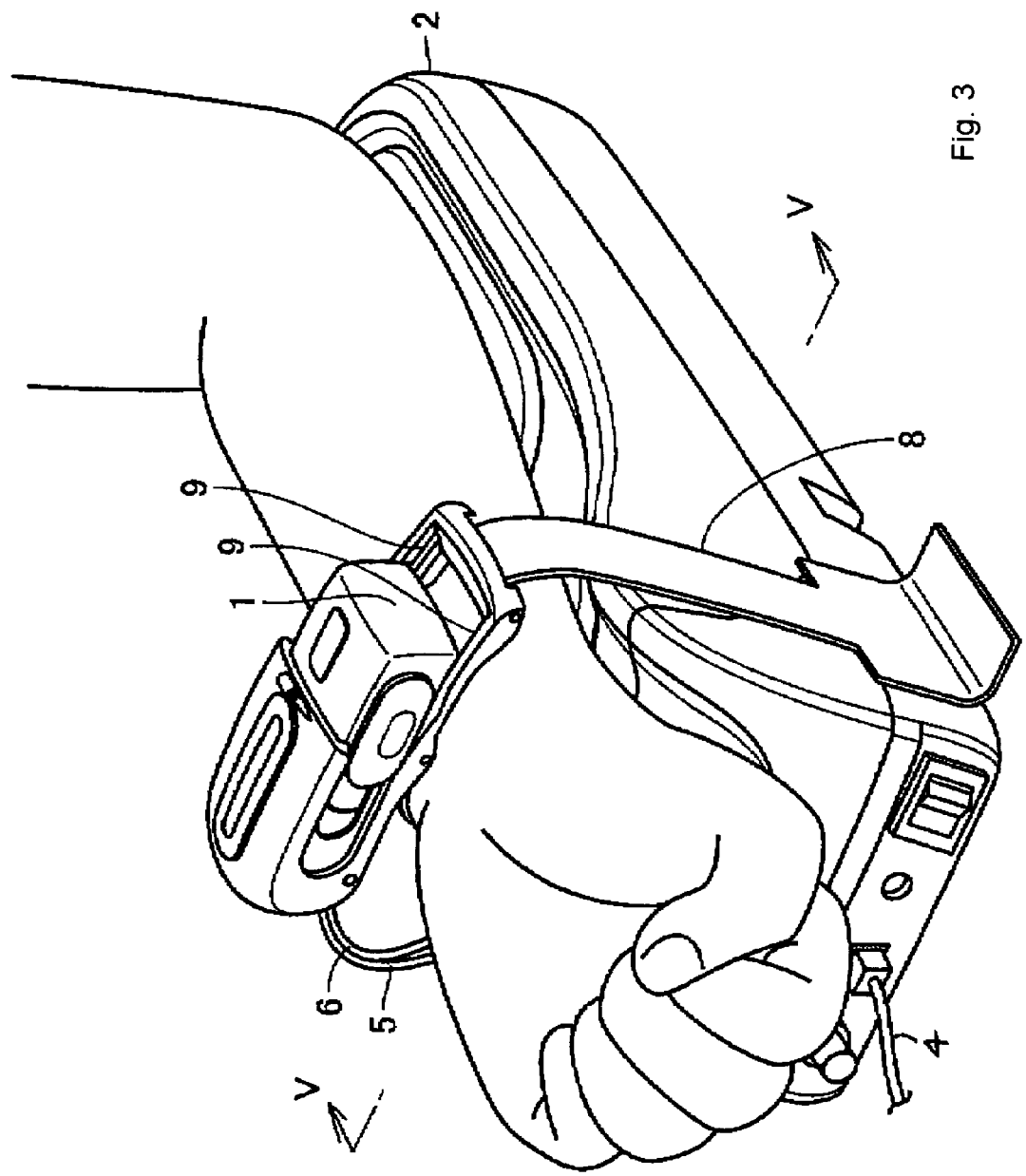
FIG. 3 shows a view of a way of use when a pulse wave is measured relating to an embodiment of the invention.

In FIG. 1, there is shown a functional architecture of a pulse wave detecting apparatus relating to an embodiment of the invention. In FIG. 2, there is shown a relationship of connection between a sensor unit and a fixing stand. In FIG. 3, there is shown a state where a pulse wave detecting apparatus is mounted on a living human body. In FIGS. 2 and 3, the pulse wave detecting apparatus includes: a sensor unit 1 mounted on a surface of a wrist for detecting a pulse wave in an artery of the wrist; a fixing stand 2 for fixing the wrist for detecting a pulse wave; and a PC (Personal Computer) unit 3 (not shown) for executing various kinds of processing including an arithmetic operation for detecting a pulse wave. In FIG. 2, the sensor unit 1 is accommodated in a case and in FIG. 3 and there is shown a state where the sensor unit 1 is moved out by sliding from the interior of the case to outside through sliding grooves 9 (see FIG. 2) and located on a wrist.

The fixing stand 2 has a fixing stand unit 7 therein and the fixing stand unit 7 and the PC unit 3 are communicably connected therebetween through a USB (Universal Series Bus) cable 4. The fixing stand unit 7 and the sensor unit 1 are connected to each other through a communication cable 5 and an air tube 6.

In a case where a pule wave is detected, the sensor unit 1 is moved by sliding and positioned on a body surface above an artery of a wrist in a state where the wrist of a user is placed at a predetermined position on the fixing stand 2 and the case of the sensor unit 1 and the fixing stand 2 are fastened with a belt 8 to fix the sensor unit 1 on the wrist so as not to be displaced.

In FIG. 1, the sensor unit 1 includes: an LED section 10 constructed of: plural LEDs (Light Emitting Diode) in parallel arrangement and provided so that the light emitting state thereof can be visually recognized from outside while mounted on the wrist; a pressure sensor array 11 of a structure in which plural pressure sensors each constructed of a diaphragm and a resistance bridge circuit for detecting a pulse pressure are disposed on a pressurization surface 40 later described in one length direction on a semiconductor chip made of a single crystal silicon or the like; a multiplexer 12 selectively deriving voltage signals outputted by plural pressure sensors in the pressure sensor array 11; and a pressurization cuff 13 including an air bag adjusted in pressure for pressing the pressure sensor array 11 against the wrist. The LED section 10 is provided in order to notify a user by light emission of information (a position of the artery or a position of a hard member such as a tendon or the like) for guiding a sliding direction of the sensor unit 1 as described later. Therefore, a means for notifying the information may also be an LCD (Liquid Crystal Display) with not limiting to LEDs.

The fixing stand unit 7 includes: a positive pressure pump 14 for raising an internal pressure (hereinafter referred to as a cuff pressure) of the pressurization cuff (air bag) 13 and a negative pressure pump 15 lowering the internal pressure; a change-over valve 16 making change-over in order to selectively connect one of the positive pressure pump 14 and the negative pressure pump 15 to the air tube 6; a control circuit 17 controlling the change-over valve 16; a communication circuit 18 to which the USB cable 4 is connected; and an A/D (Analog/Digital) converter 19 for converting an output signal derived from the sensor unit 1 to digital data.

The PC unit 3 includes: a CPU (Central Processing Unit) 20 executing various kinds of processing including an arithmetic operation for controlling a pulse wave detecting apparatus in a concentrated manner; a ROM (Read Only Memory) 21 and a RAM (Random Access Memory) 22 storing a data and a program for controlling the pulse wave detecting apparatus; an operation section 23 provided operable from outside and being operated for inputting various kinds of information; and a display unit 24 made of an LCD or the like for outputting various kinds of information such as a result of detection of a pulse wave and the like to outside.

Note that while the fixing stand unit 7 of the fixing stand 2 and the PC unit 3 here are separately provided, both functions may be incorporated in the fixing stand 2.

Figure 4:
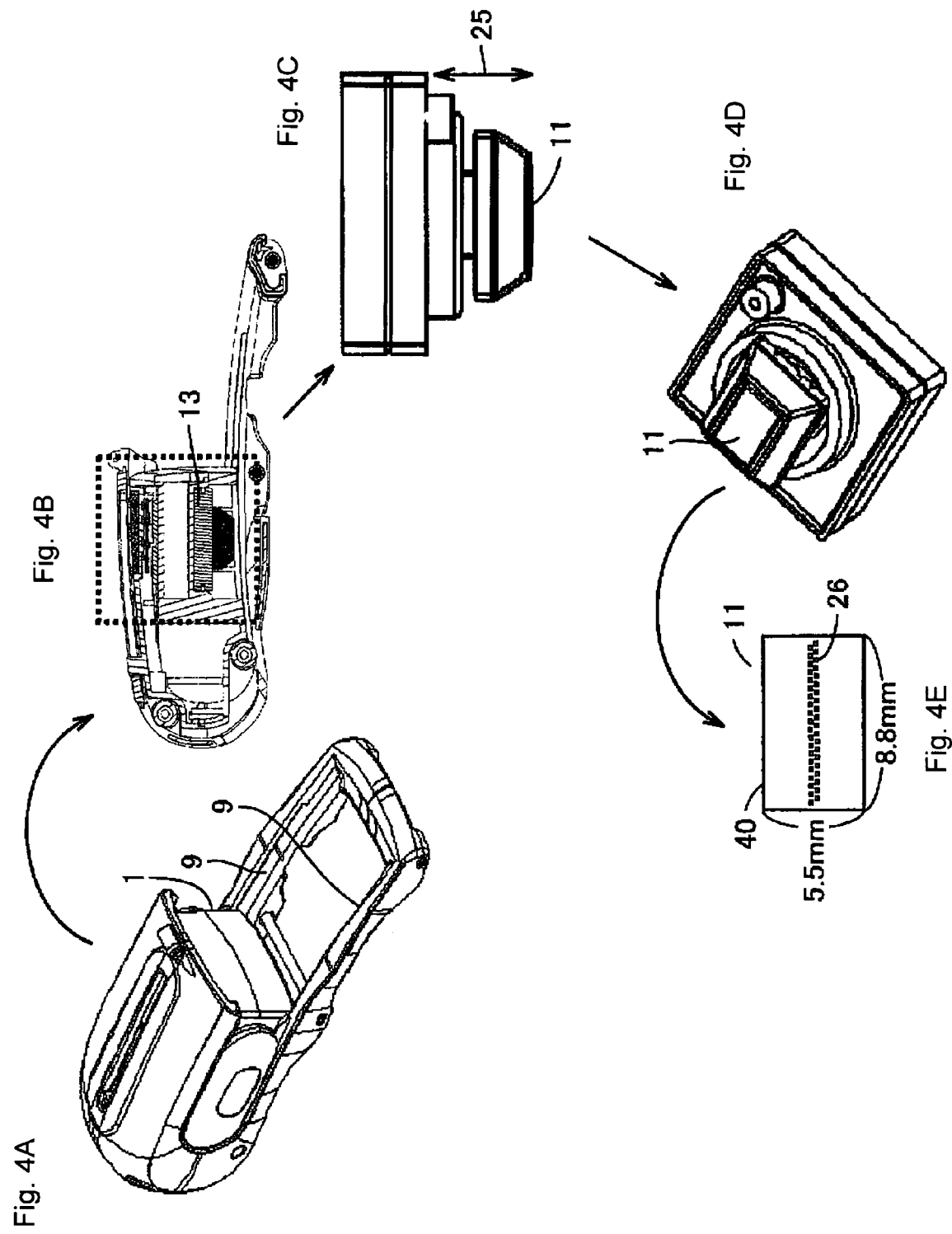
FIGS. 4A to 4E show views of a structure of a pressure sensor array of a sensor unit relating to an embodiment of the invention.

In FIGS. 4A to 4E, there is shown a structure of the sensor unit 1. In FIG. 4B, there is shown a sectional structure of the sensor unit 1 of FIG. 4A taken on a direction traversing a wrist when being mounted on the wrist. In FIG. 4C, there is shown an enlarged view of a part in a frame enclosed with broken lines of FIG. 4B. When the pressurization cuff 13 of FIG. 4B is adjusted in cuff pressure with the positive pressure pump 14 and the negative pressure pump 15, the pressure sensor array 11 attached with a block molded with ceramic or resin interposed therebetween is freely moved in a direction of an arrow mark 25 shown in FIG. 4C by a distance corresponding to the cuff pressure level. The pressure sensor 11 is moved downward along the direction of an arrow mark 25, thereby, protruded from an opening formed in advance in the case to outside and pressed against a surface of the wrist. The disposing direction of plural pressure sensors 26 of the pressure sensor array 11, as shown in FIGS. 4D and 4E, corresponds to a direction intersecting with an artery at an almost right angle when the sensor unit is mounted on a wrist and a length of disposition is longer than at least a diameter of the artery. If the pressure sensors 26 are pressed against the wrist by a cuff pressure of the pressurization cuff 13, a pressure sensor 26 outputs pressure information, which is a pressure oscillating wave generated in an artery and transmitted to a living human body surface, as a voltage signal. The pressure sensors 26, for example, in number of 40 pieces, are disposed on the pressurization surface 40 of a predetermined size (5.5 mm×8.8 mm).

Figure 5:
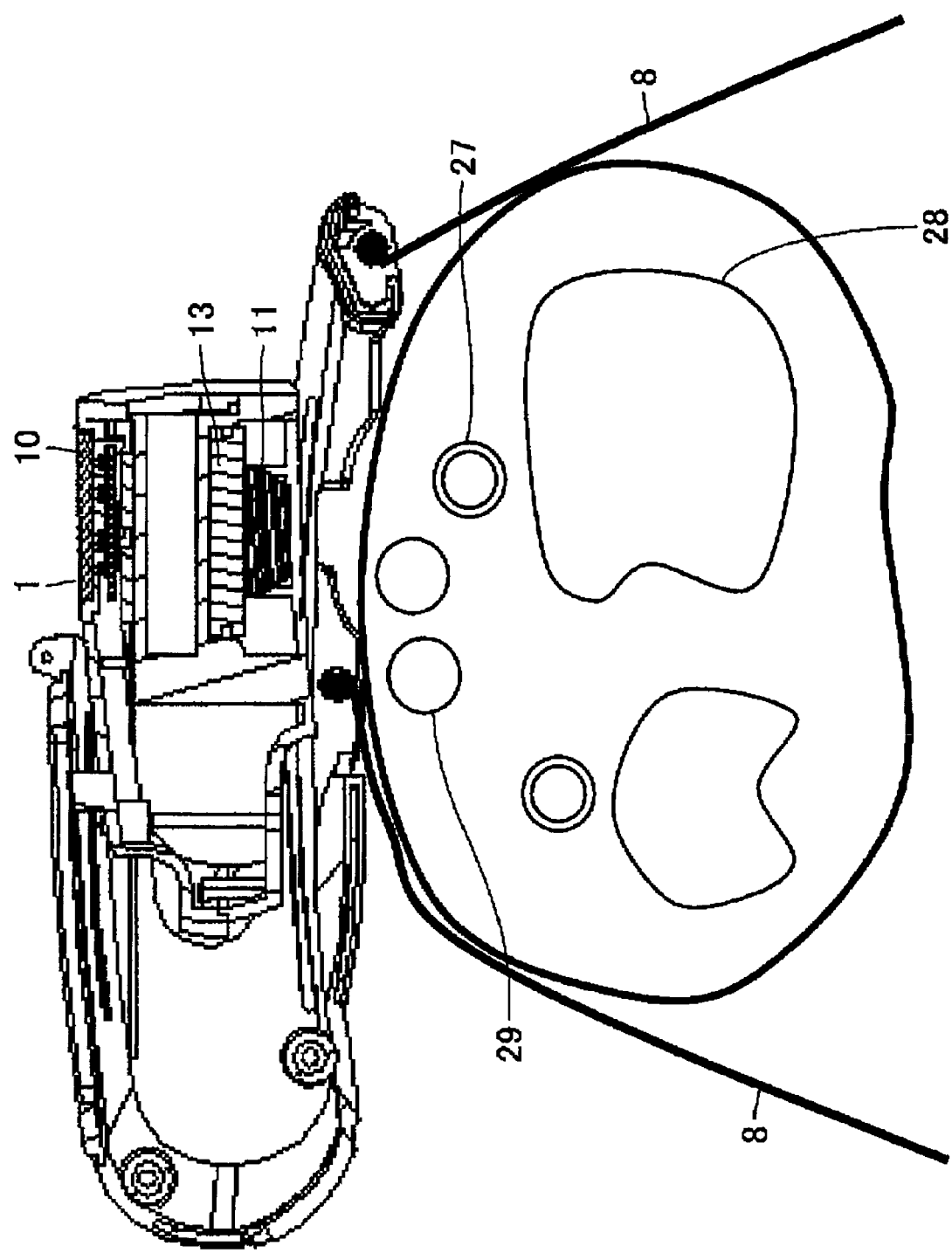
FIG. 5 shows a view of a section taken on line V—V of FIG. 3.

In FIG. 5, there is shown a view of a section taken on line V—V of FIG. 3. Since, in FIG. 5, a cuff pressure of the pressurization cuff 13 is sufficiently lowered by the negative pressure pump 15 (at an pressure level sufficiently lower than the atmospheric pressure), the pressure sensor array 11 is in a state to be accommodated in the case of the sensor unit 1 in no contact with the surface of a wrist.

Included in a wrist are a radial artery 27 for detecting a pulse wave and hard members such as a radius 28 near the radial artery 27 and a tendon 29. When a pulse wave is detected on a surface of a wrist above a hard member, an artifact pulse wave is included in a detected pulse wave.

In this embodiment, in order to detect a pulse wave from which an artifact pulse wave is removed, pressure sensors 26 left after the pressure sensor 26 located above a hard member is excluded are selected as candidates for the pressure sensor 26 located above the radial artery 27, an optimal pressure sensor 26, that is the pressure sensor 26 located above the radial artery 27 is specified among the candidates pressure sensors 26 and pressure information of the specified pressure sensor 26 is used to detect a pulse wave.

A position of a hard member or the radial artery 27 is notified to a user and the user causes the sensor unit 1 to slide in a direction toward the radial artery 27 according to the contents of the notification. Description will be given of details of the notification later.

Description will be given of a procedure of processing for detecting a pulse wave according to this embodiment following a flowchart of FIG. 6. A program instructing the flowchart and data referred to when the program runs are stored in advance in ROM 21 and RAM 22 and CPU 20 reads out and executes the program while referring to the data when required to thereby cause a pulse wave detecting processing to be advanced.

First of all, when a user turns on a power supply switch (not shown), CPU 20 commands the control circuit 17 through the communication circuit 18 so that the negative pressure pump 15 is driven; therefore, the control circuit 17 changes over the change-over valve 16 to the negative pressure pump 15 side based on the command to drive the negative pressure pump 15 (S1).

Since the negative pressure pump 15, in a case where being driven, acts so that a cuff pressure is rendered sufficiently lower than the atmospheric pressure through the change-over valve 16, the pressure sensor array 11 moves upwardly in the direction of an arrow mark 25 of FIG. 4C. As a result, it can be avoided that the pressure sensor array 11 is protruded carelessly, resulting in a malfunction and a failure.

Thereafter, when a user turns on a start button (not shown) after mounting the sensor unit 1 onto a wrist as in FIG. 3, it is determined whether or not the pressure sensor array 11 has moved, that is the sensor unit 1 has moved by sliding along the slide grooves 9 so as to be located on a surface of the wrist (S2). A micro-switch not shown for detecting sliding movement is provided in the case of the sensor unit 1 and CPU 20 determines whether or not the pressure sensor array 11 has moved based on a detection signal of the micro-switch.

Till it is determined that the pressure sensor array 11 has moved (NO in S2), the processing in S1 is repeated, while if it is determined that the pressure sensor array 11 has moved (YES in S2), CPU 20 commands the control circuit 17 so as to drive the positive pressure pump 14 through the communication circuit 18; therefore, the control circuit 17 changes over the change-over valve 16 to the positive pressure pump 14 side based on the command to drive the positive pressure pump 14 (S3). Thereby, a cuff pressure rises and the pressure sensor array 11 moves downward in the direction of an arrow mark 25 of FIG. 4C to thereby press the pressure sensor array 11 against a surface of a wrist.

In a case where the pressure sensor array 11 is pressed against the surface of a wrist (see FIG. 5), pressure information of voltage signals from the pressure sensors 26 is derived through the multiplexer 12, converted by the A/D converter 19 into digital information and supplied to CPU 20 through the communication circuit 18. CPU 20 prepares a tonogram using the digital information to display the tonogram on the display unit 24 (S4) Description will be given of details of the prepared (displayed) tonogram later.

The, CPU 20 executes processing excluding a hare member such as a tendon 29 or the radius 28 based on the tonogram (S5). In the hard member excluding processing, the pressure sensor 26 located above the hard member in the pressure sensor array 11 is specified based on information on the tonogram obtained in S4 and pressure sensors 26 left after the specified pressure sensor 26 is excluded are selected as candidates for the pressure sensor 26 located above the radial artery 27. Description is given of details of the selection later.

Then, CPU 20 executes processing for selecting the pressure sensor 26 located above the radial artery 27 as an optimal channel from the candidates of the pressure sensor 26 located above the radial artery 27 (S6). Description will be given of details of the optimal channel selecting processing later.

Then, CPU 20, in order to detect a pulse wave based on pressure information inputted from the pressure sensor 26 corresponding to the selected optimal channel, calculates an amount of a change in pressurization pressure level by the pressurization cuff 13 to compare the amount of a change with a predetermined amount of a change at which a pulse wave can be detected (S7). As a result, if the calculated amount of a change meets the predetermined amount of a change, it is determined that a cuff pressure condition for detecting a pulse wave is met (YES in S8), while if not meet, processing from S4 to S8 is repeated till the cuff pressure condition is met with continued pressurization imposed on the pressurization cuff 13 by the positive pressure pump 14.

In a case where the cuff pressure condition is met (YES in S8), the positive pressure pump 14 is adjusted so that a pressurization level to the pressure array sensor array 11 by the pressurization cuff 13 is an optimal level for detecting a pulse wave (S9). Description will be given of details of the optimal pressure adjusting processing later.

In a state where the optimal pressure adjustment is conducted in the pressurization cuff 13, pressure information outputted by a selected pressure sensor 26 as an optimal channel, that is waveform data of a pulse wave of the radial artery 27 is transferred to CPU 20 through the multiplexer 22, the A/D converter 19 and the communication circuit 18 (S10).

CPU 20 receives waveform data to detect a pulse wave based on the received waveform data. The transfer processing of waveform data in S10 is repeated till it is determined that the waveform data is received and a predetermined condition for the end of detection of a pulse wave has been established. Note that the pulse wave detecting processing based on received waveform data is conducted according to a known procedure; therefore description of details thereof is omitted here.

When the predetermined condition for the end of detection of a pulse wave is established (YES in S11), CPU 20 controls the negative pressure pump 15 to be driven through the change-over valves 16 (S12). By doing so, a pressurization state of the pressure sensor array 11 against a wrist is cancelled to end a series of operations in the pulse wave detecting processing.

CPU 20 outputs information on a detected pulse wave to outside through the display unit 24 or the like. Instead of information on a pulse wave, AI (Augmentation Index) obtained by calculation using the information on a pulse wave may also be outputted.

Description will be given here of an output characteristic of the pressure sensor 26. In this embodiment, CPU 20 acquires voltage signals outputted by the respective pressure sensors 26 simultaneously along the time axis through the multiplexer 12, the DC components and the AC components corresponding to pulse wave components are obtained from the acquired voltage signals of the respective pressure sensors 26 and positions of the radial artery 27 and a hard member (a tendon 29 or a radius 28) are recognized based on the characteristics.

A DC component is obtained based on the average value in a predetermined time of a voltage signal (for example, one beat period), a component passing a low pass filter of a voltage signal (a component left after a pulse wave is removed) or a voltage signal level at a pulse wave rising point (just before a pulse component is mixed in). An AC component includes components of a pulse wave of the radial artery 27 and an artifact pulse wave. The AC component is obtained by deriving at least through a filter processing of a component in a predetermined frequency band (for example, 0.5 to 25 Hz) of a pulse wave of the radial artery 27.

Figure 7:
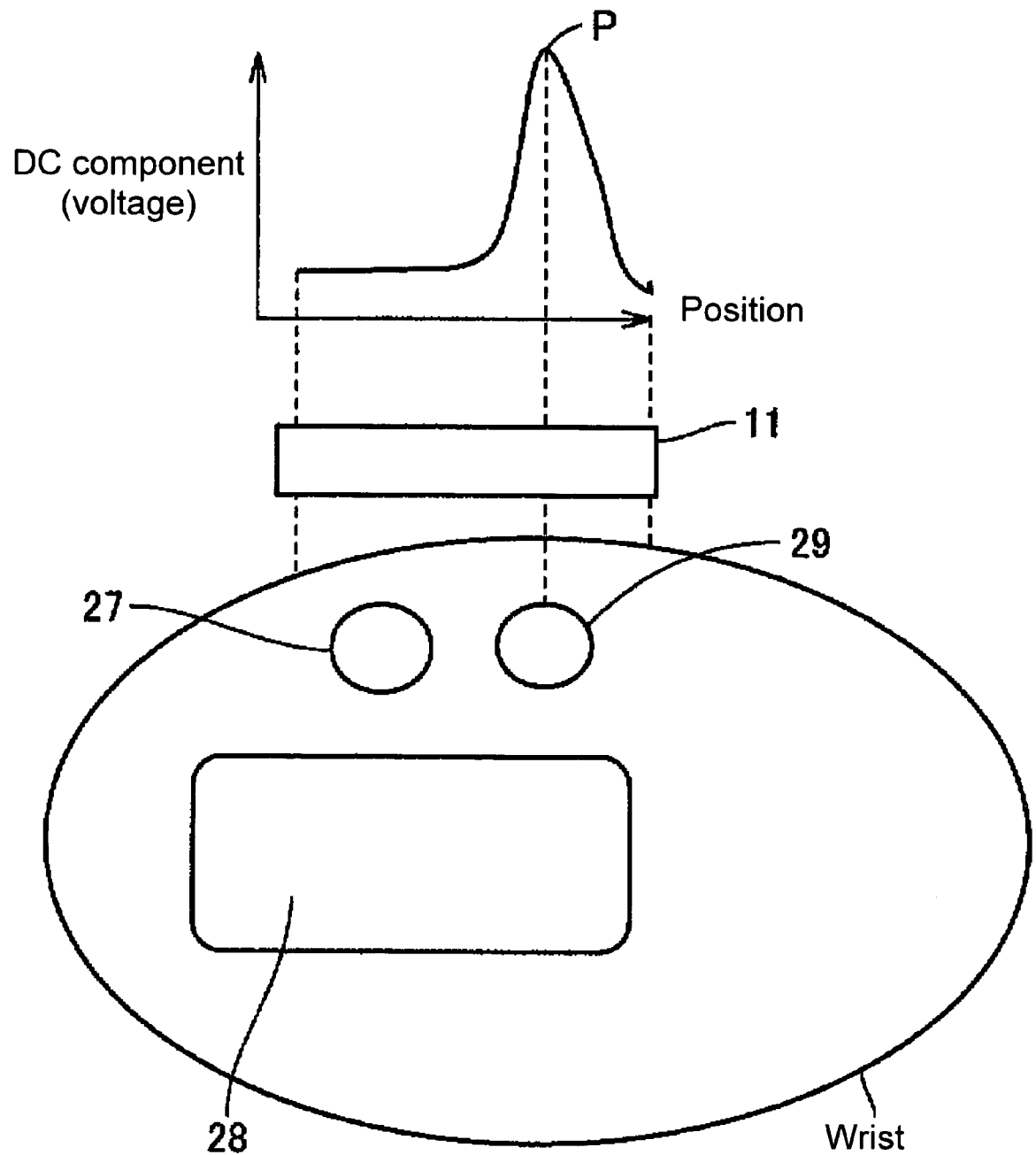
FIG. 7 shows a representation of a characteristic of a DC component of an output of a pressure sensor array.
Figure 8:
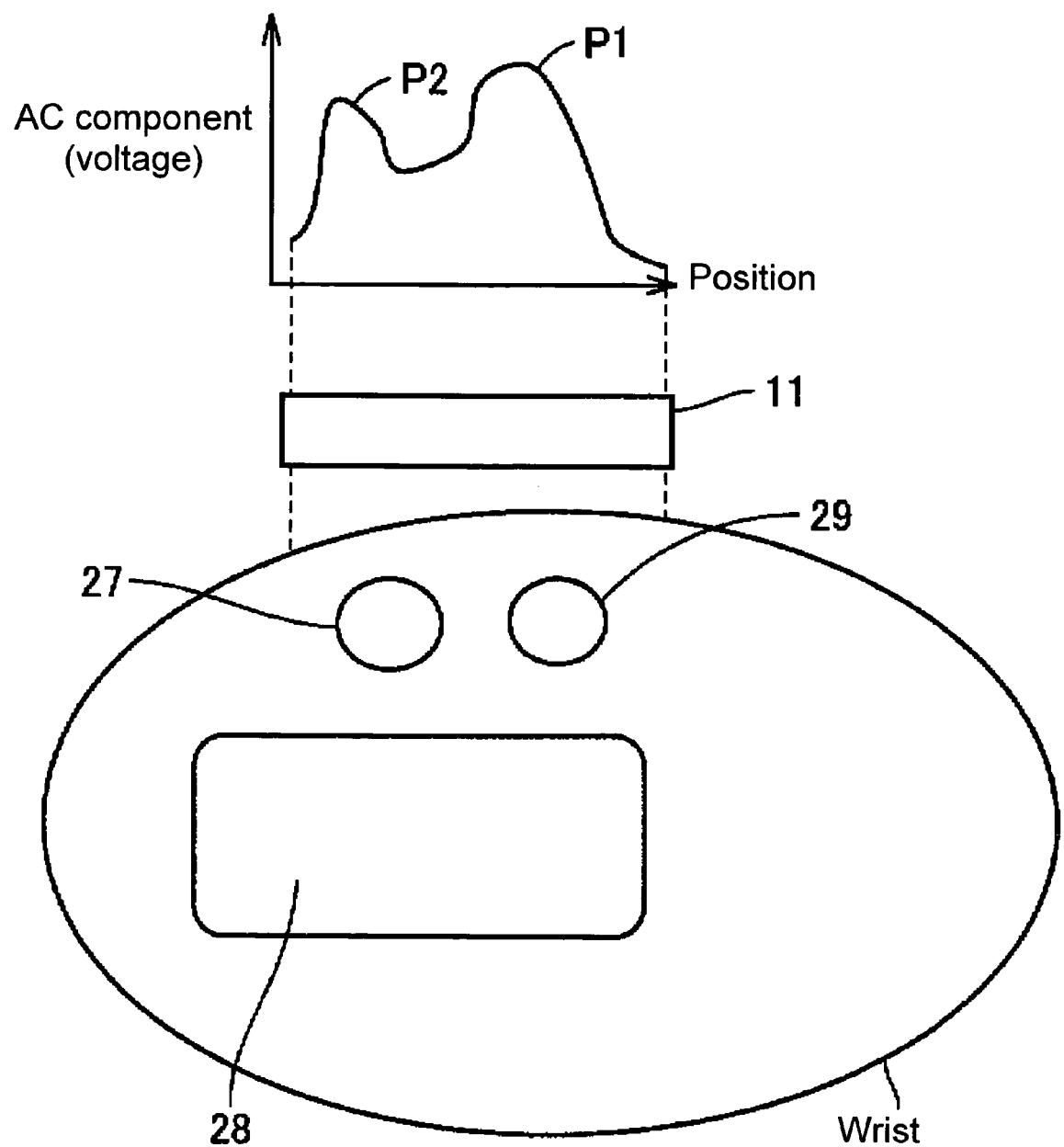
FIG. 8 shows a representation of a characteristic of an AC component of an output of a pressure sensor array.

In FIGS. 7 and 8, there are shown characteristics of the DC component and the AC component of a voltage outputted by a pressure sensor 26 as models in a state where the pressure sensor array 11 is located on a surface of a wrist to detect a pulse wave. In the tonograms depicted on the upper parts of FIGS. 7 and 8, the abscissa are assigned to positional data of pressure sensors 26 disposed intersecting with the radial artery 27 at an almost right angle in the pressure sensor array 11. In the tonogram of FIG. 7, the ordinate are used for plotting data of the DC components of voltage signals outputted from the pressure sensors 26 and in the tonogram of FIG. 8, the ordinate are used for plotting data of the AC components of voltage signals outputted from the pressure sensors.

As can be seen from the tonogram of FIG. 7, since information showing a component of a pressure generated by a hard member (tendon 29) included in pressure information, that is the DC component of a voltage signal, outputted from the pressure sensor 26 located above the hard member (tendon 29) among plural pressure sensors 26 in disposition, is higher than the DC component levels outputted from the other pressure components 26, the information generated by the hard member indicates the highest level shown by a peak point P among the DC component levels. Accordingly, it is specified that the pressure sensor 26 of positional data corresponding to the peak point P is located above a hard member.

In this way, hard member position information indicating the pressure sensor 26 located at a position of or above the hard member can be obtained based on information indicating a pressure component generated, that is the DC component of a voltage signal outputted, by a hard member (tendon 29) of pressure information outputted from plural pressure sensors 26.

Levels of AC components of the pressure sensors 26 shown in the graph of FIG. 8 show changes in voltage in a predetermined time (amplitudes of pulse waves) outputted from the pressure sensors 26. In the graph of FIG. 8, AC components levels of the pressure sensor 26 located above the tendon 29, which is a hard member, and the pressure sensor 26 located above the radial artery 27 are indicated by respective two peak points P1 and P2, higher and lower. This is because a waveform obtained by inverting a waveform of a pulse wave is observed. Description will be given of details thereof with reference to FIGS. 9 and 10.

Figure 9:
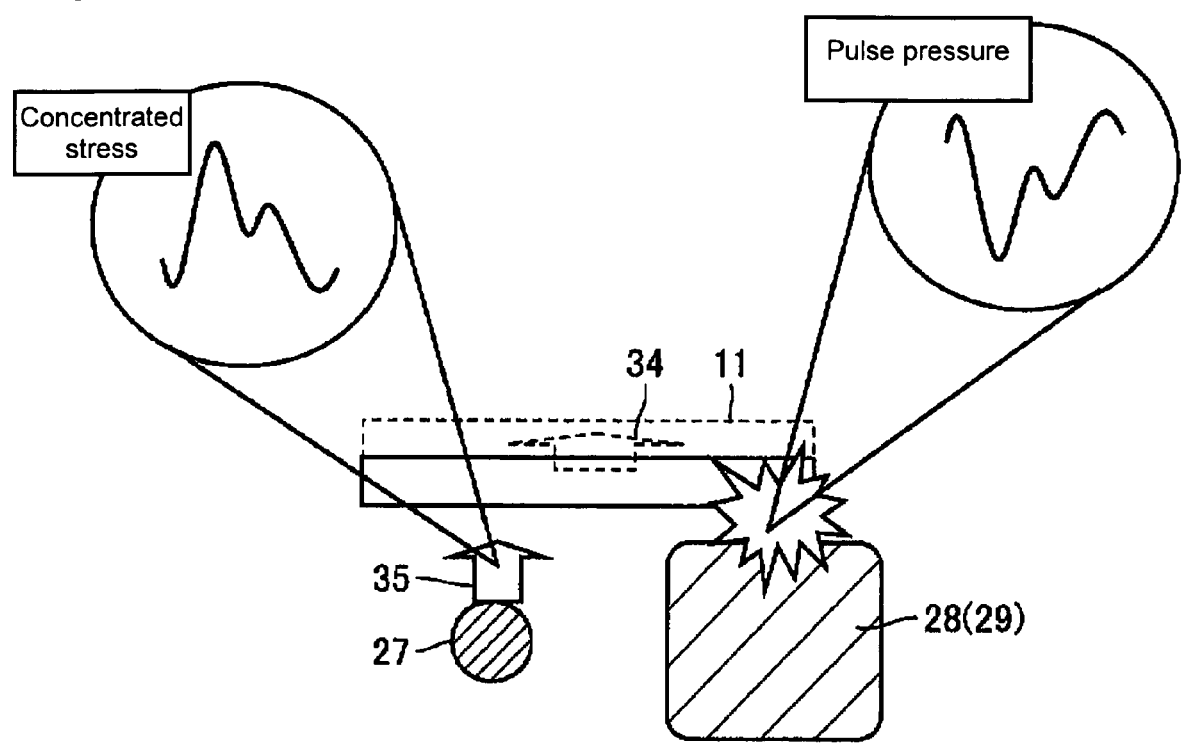
FIG. 9 shows a representation of a mechanism of occurrence of an inverted pulse wave.

As shown in FIG. 9, a force acts on the pressure sensor array 11 in a direction of an arrow 34 by a pulse pressure transmitted in a direction of an arrow 35 of the radial artery 27 and a concentrated stress acts on the pressure sensor 26 located above a hare member of the radius 28 (or the tendon 29) as a reaction of the force in the direction of an arrow 34. As a result, a noise component caused by the concentrated stress, that is an artifact pulse wave, is mixed into the AC component outputted by the pressure sensor 26 located above the radius 28 (the tendon 29). Since the artifact pulse wave has a waveform obtained by inverting a pulse wave detected in the artery 27, the pulse wave is referred to inverted pulse wave. The inverted pulse wave, when a pulse wave is detected, is detected in error as a signal of a pulse wave from the radial artery 27.

Figure 10:
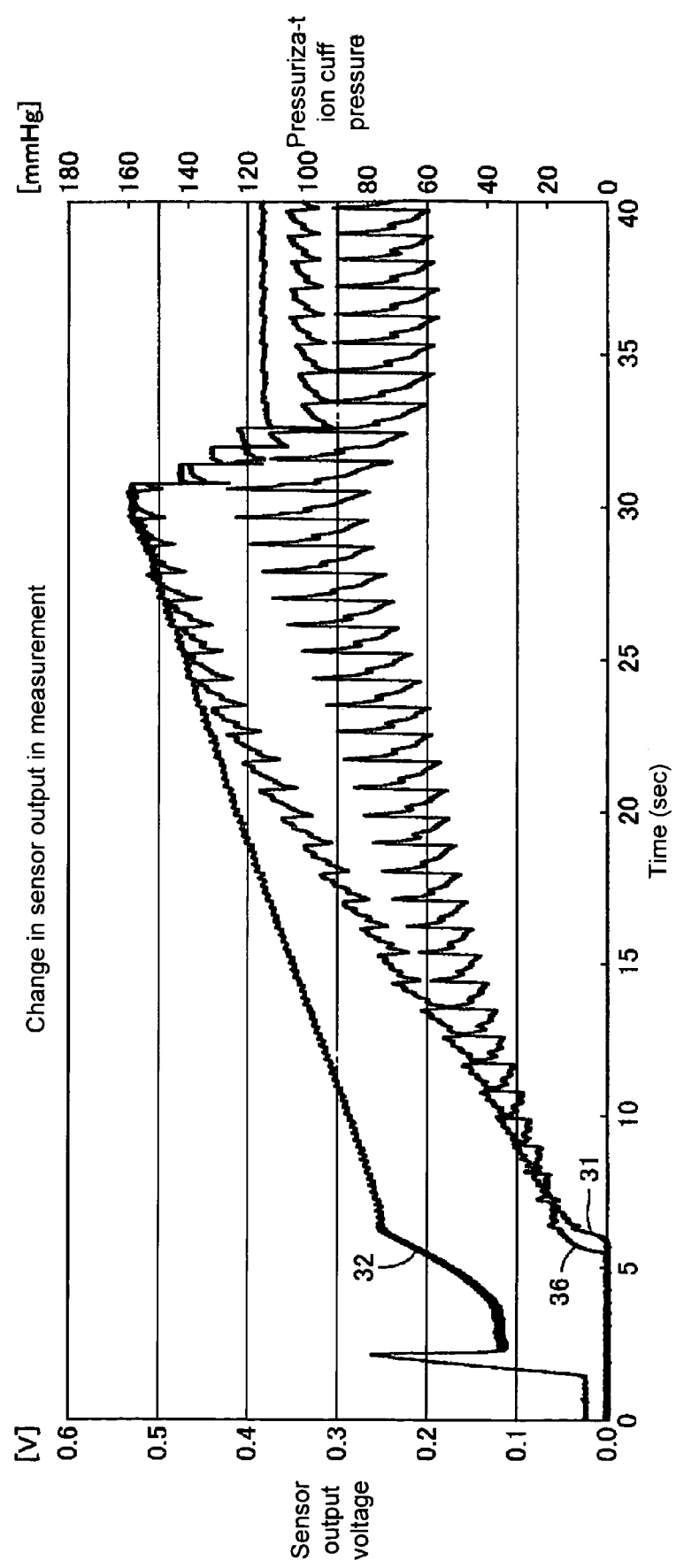
FIG. 10 shows a graph of an example in which an inverted pulse wave is observed as an output signal from a pressure sensor during a pulse wave measurement.

Description will be given of an inverted pulse wave with reference to a graph of FIG. 10. FIG. 10 shows a change in output of a pressure sensor 26 during a pulse wave measurement. The ordinate of the graph are used for plotting a voltage signal level outputted by a pressure sensor 26 and a pressurization pressure level in the pressurization cuff 13 against the pressure sensor array 11 and the abscissa is assigned to elapsed time in pulse wave measurement. As a pressurization pressure level is gradually raised with elapse of time, not only is a waveform 31 originating from a pulse pressure in the radial artery detected, but a waveform 36 of a signal outputted from a pressure sensor located above the radius 28 (tendon 29) is also detected as shown in FIG. 9. The waveform 36 is an inverse of the pulse wave waveform 31. As is seen by comparison of the pulse wave waveform 31 with the waveform 36, the DC component of the waveform 36 is higher than that of the pulse wave component 31 since the waveform 36 is caused by a hard member despite of a pressurization force in the pressurization cuff 13 being equal.

Since, in this way, an artifact pulse wave component is mixed into pressure information outputted from a pressure sensor 26, it is difficult to surely specify the pressure sensor 26 located above the radial artery 27 based only on an AC component (a pulse wave amplitude) of FIG. 8. Therefore, in this embodiment, a pressure sensor 26 located above the radial artery 27 is specified as shown in FIG. 11.

Figure 11:
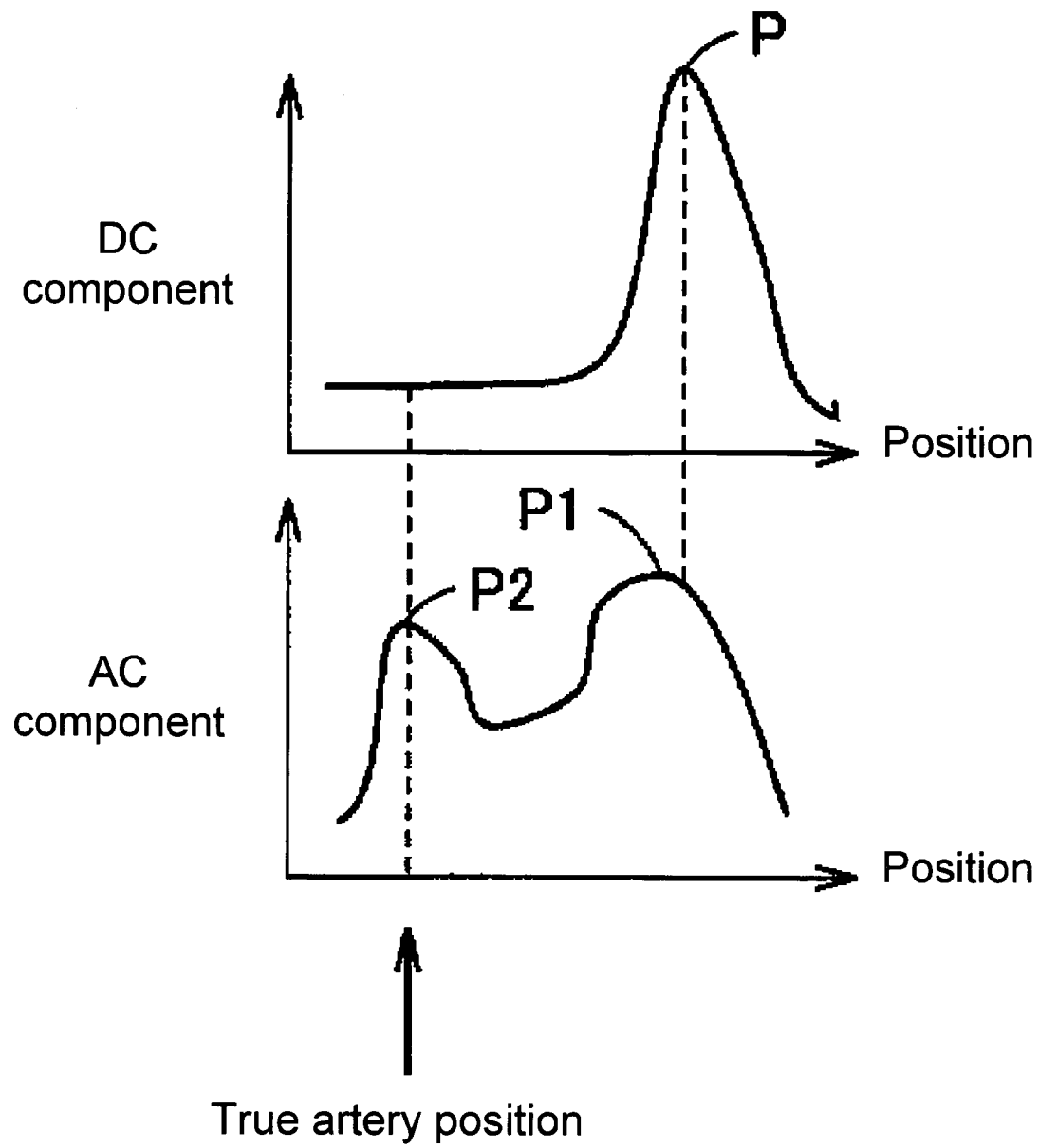
FIG. 11 shows graphs of characteristics of a DC component and an AC component of a pressure sensor array output adopting the same X axis assigned to a position.

In FIG. 11, the tonogram of the DC components of FIG. 7 and the tonogram of the AC components of FIG. 8 are shown with the abscissas assigned to a position axis on the same scale. With reference to both tonograms, it is determined that if a DC component level is higher, though with a corresponding AC component (pulse wave amplitude) higher in level, the AC component is considered to be raised by including an artifact pulse wave; therefore, it can be determined that a pressure sensor 26 with a corresponding lower DC component level and a corresponding AC component (pulse amplitude) as a peak has a very high possibility of being located above the radial artery 27.

(Hard Member Excluding Processing and Optimal Channel Selecting Processing)

In the hard member excluding processing (S5) and the optimal channel selecting processing (S6) of FIG. 6, CPU 20 extracts the DC components from voltage signals of pressure information from the respective pressure sensors 26 based on the characteristics shown in FIGS. 7 to 11 as shown in the following example processing 1 to 4, specifies the pressure sensor 26 located above a hard member from the extracted DC components, excludes an output from the specified pressure sensor 26 and selects the other pressure sensors 26 left after the specified pressure sensor 26 is excluded as candidates for the pressure sensor 26 located above the radial artery 27.

Figure 14:
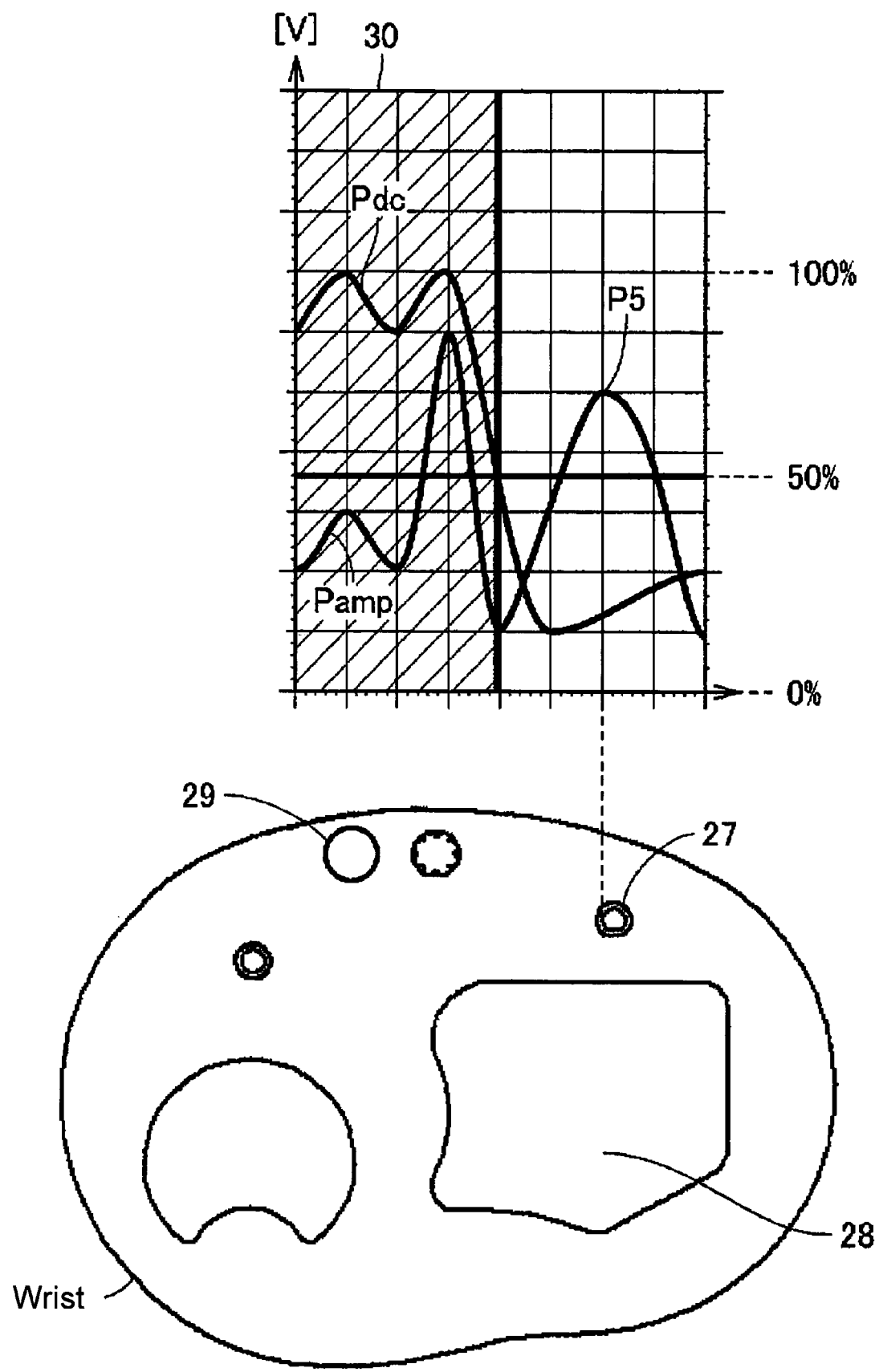
FIG. 14 shows a representation of still another example of a procedure in processing specifying a sensor as an optimal channel from output characteristics of a pressure sensor array relating to an embodiment of the invention.

Description will be given of the example processing 1 to 3 with reference to FIGS. 12 to 14. The tonograms depicted in the upper parts in FIGS. 12 to 14 are prepared in S4 of FIG. 6 and displayed. The abscissas of the tonograms are assigned to position data of plural pressure sensors 26 disposed on a wrist a section of which is shown in the lower parts of the figures and the ordinates thereof are used for plotting levels of AC components Pamp corresponding to pulse wave amplitude information based on output voltage signals from the respective pressure sensors 26, DC components Pdc indicating hard member information and pulse wave components Part indicating artery position information. Note that in the graph of FIG. 14, no pulse wave component Part is shown.

EXAMPLE PROCESSING 1

CPU 20 obtains a pulse wave component Part by normalizing an AC component Pamp with a DC component Pdc using an arithmetic expression of (Part=Pamp/Pdc). By doing so, a pressure sensor 26 corresponding to a position data of a pulse wave component Part at a low level is specified to be located above a hard member. The pressure sensors 26 left after the specified pressure sensor 26 is excluded, that is pressure sensors 26 each having a DC component Pdc at a lower level and an AC component Pamp at a higher level is selected as candidates for the pressure sensor 26 located above the radial artery 27. CPU 20 selects the pressure sensor 26 of position data corresponding to a peak point P3 of the pulse wave components Part among the pressure sensors 26 as an optimal channel for detecting a pulse wave located above the radial artery 27.

EXAMPLE PROCESSING 2

In this example processing, CPU 20 obtains a pulse wave component Part shown in the graph of FIG. 13 by subtraction using an arithmetic expression of (Part=αPamp−βPdc), wherein α and β are constants determined by a sensitivity of pressure sensors 26.

With this expression adopted, a pressure sensor 26 corresponding to position data at which a pulse component Part is at a low level is specified that it is likely to be located above a hard member. Pressure sensors 26 left after the specified pressure sensor 26 is excluded, that is pressure sensors 26 each having a DC component Pdc at a lower level and an AC component Pamp at a higher level, are selected as candidates for the pressure sensor 26 located above the radial artery 27. CPU 20 selects a pressure sensor 26 at position data corresponding a peak point P4 of pulse wave components Part among the pressure sensors 26 of the candidates as an optimal channel for detecting a pulse wave located above the radial artery 27.

EXAMPLE PROCESSING 3

In this example processing 3, CPU 20 specifies all of pressure sensors 26 each having a DC component Pdc at a level of a given threshold or higher as ones not located above the radial artery 27. CPU 20 regards the pressure sensors 26 left after the specified pressure sensors 26 as candidates for the pressure sensor 26 located above the radial artery 27 and selects a pressure sensor 26 having a DC component Pdc at a lower level and an AC component Pamp at a higher level as an optimal channel.

To be concrete, all of pressure sensors 26 each outputting a DC component Pdc at a level exceeding 50% of the maximum value of DC components Pdc which are included in a hatched region 30 of FIG. 14 are excluded and the pressure sensors 26 left after the exclusion corresponding to position data included in the other region than the region 30 are regarded as candidates for the pressure sensor 26 located above the radial artery 27. A pressure sensor 26 showing a level at a peak point P5 of AC components Pamp is determined as a pressure sensor 26 located above the radial artery 27 to select it as an optimal channel.

In the example processing 3, while the threshold value for specifying the region 30 is 50% of the maximum value of DC components Pdc, the threshold value is not limited to this value.

Figure 6:
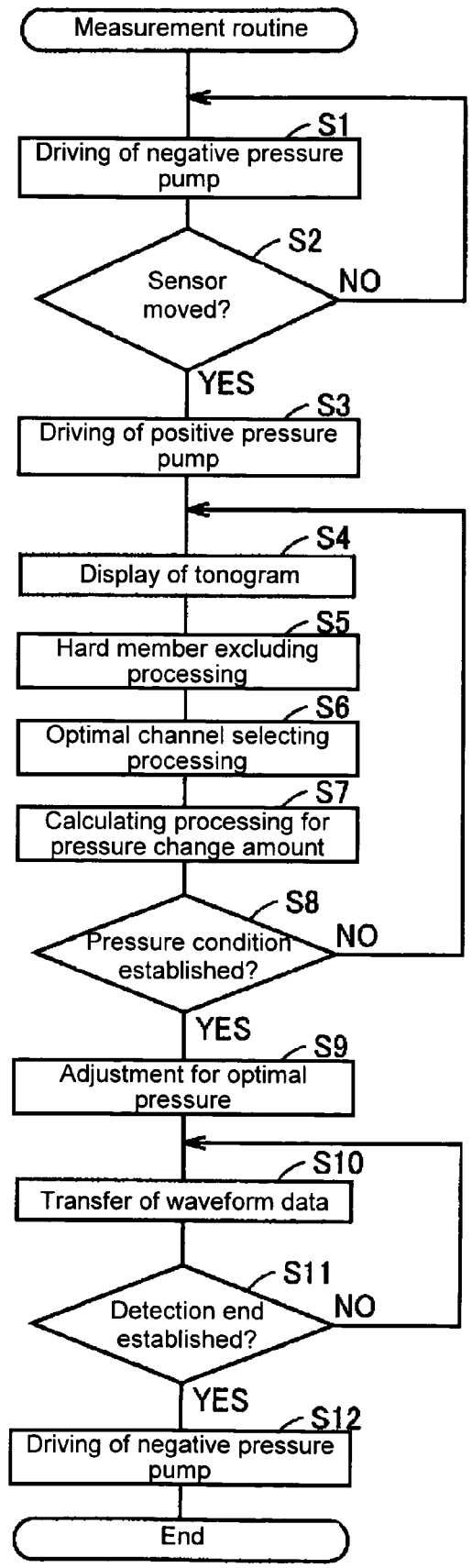
FIG. 6 shows a flowchart of processing for pule wave measurement relating to an embodiment of the invention.

While the tonograms of FIGS. 12 to 14 are prepared and displayed on the display unit 24 in S4 of FIG. 6, the tonograms may be displayed only in a case where a user inputs a request for a display of a graph through the operation section 23. In the tonograms of FIGS. 12 to 14, values plotted for respective pressure sensors 26 are stored in RAM 22 in the form of a table being associated with the pressure sensors 26 and CPU 20 executes processing in S5 and S6 based on information in the table in RAM 22.

EXAMPLE PROCESSING 4

The hard member excluding processing (S5) may also be conducted in the following way. For example, a waveform of a DC component of FIG. 7 is a curve formed by connecting DC component levels of plural pressure sensors 26 in a disposing direction and it is understood that when an attention is given to an inclination thereof, a tendon 29 is located in a direction in which an inclination thereof is larger, that is in a direction toward a peak point P. CPU 20 obtains an amount of a change in DC component in one direction of the waveform of a DC component Pdc, that is an inclination of the waveform (Pdc/dx), based on outputs of the pressure sensors 26, specifies position data at which the tendon 29 is located based on the values of the obtained inclinations and excludes a pressure sensor 26 at the corresponding position data as the pressure sensor 26 located above a hard member. In the optimal channel selecting processing (S6) thereafter, one of the example processing 1 to 3 is applied.

(Calculation of Amount of Change in Pressure and Processing in Optimal Pressure Adjustment)

Figure 15:
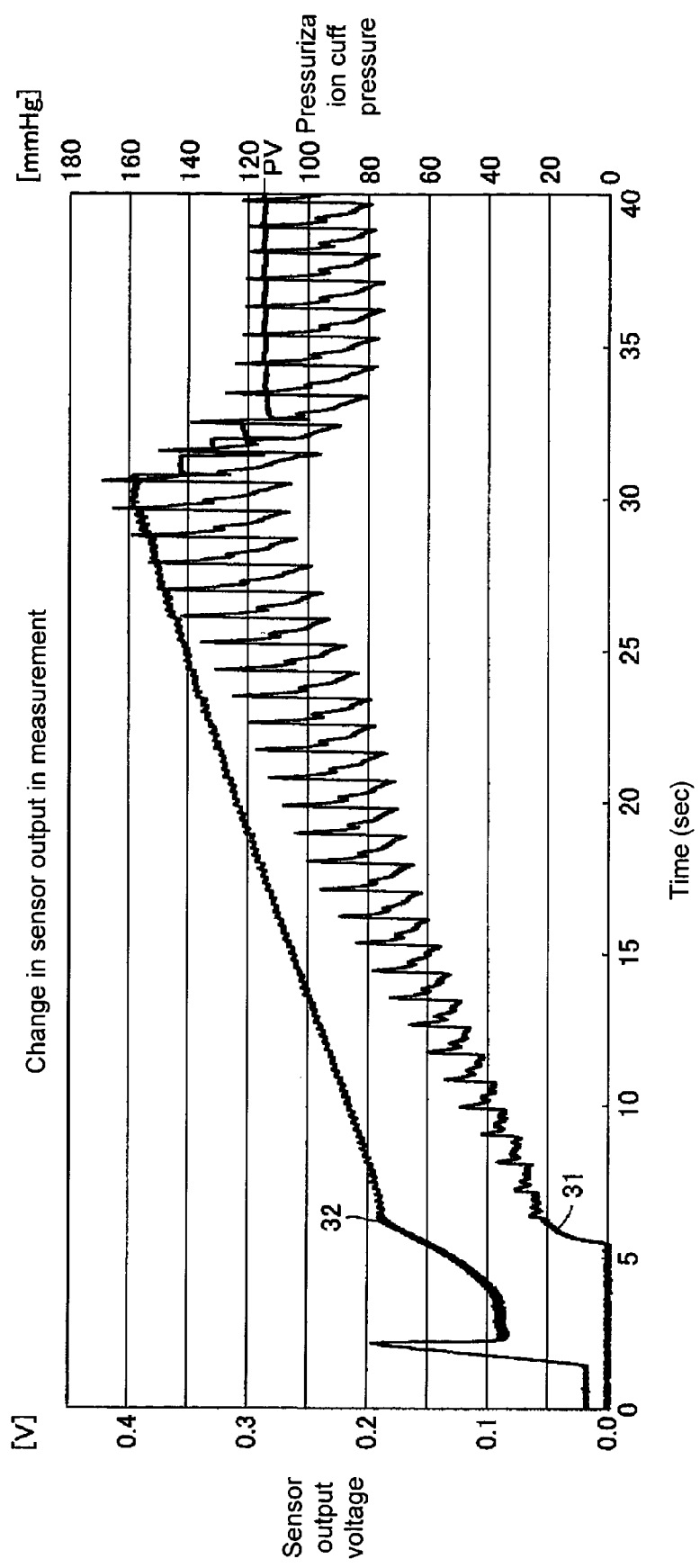
FIG. 15 shows a graph of changes in output of a sensor when a pulse wave is measured relating to an embodiment of the invention.

Description will be given of processing for calculation of an amount of a change in pressure and adjustment for optimal pressure in S7 to S9 of FIG. 6 with reference to FIG. 15. A graph of FIG. 15 shows a change in output of a pressure sensor 26 in pulse wave measurement. The ordinate is used for plotting a voltage signal level outputted from a pressure sensor 26 and a pressurization pressure level of the pressure sensor array 11 by the pressurization cuff 13 and the abscissa is assigned to elapse of time in pulse wave measurement.

A pressurization force acting on the pressure sensor array 11 caused by a cuff pressure changes continuously after a pressure sensor 26 of the optimal channel is selected in the way described above. CPU 20 inputs a voltage signal outputted from the selected pressure sensor 26 as an optimal channel while changing the pressurization force. A waveform 31 of FIG. 15 including pulse waves of an inputted voltage signal (pressure information) becomes conspicuous as a pressurization pressure level shown as a waveform 32 of a pressurization pressure in the pressurization cuff 13 rises with elapse of time.

CPU 20 determines that a pressure condition for detecting a pulse wave is established at a time point at which a pressurization pressure level caused by the pressurization cuff 13 sufficiently exceeds an optimal level (for example, at a time point near 30 sec of FIG. 15) while the pressurization pressure level is raised gradually (YES in S8). Thereafter, CPU 20 drives the change-over valve 16 to continuously adjust a pressurization pressure level till it reaches an optimal level for detecting a pulse wave. Pressure information (voltage signal) outputted from the pressure sensor 26 selected as an optimal channel during a period when a pressurization pressure level is at an optimal level (see a level PV of FIG. 15) is derived by the multiplexer 12 and given to CPU 20 through the A/D converter 19 and the communication circuit 18.

The graph of FIG. 15 may also be prepared by CPU 20 and displayed on the display unit 24.

CPU 20 sequentially inputs a pressurization pressure level shown by the waveform 32 changing with elapse of time in the graph of FIG. 15 and pressure information shown by the waveform 31 and can execute processing in S7 to S9 of FIG. 6 based on contents of the inputs.

(Indicating Processing of Sliding Direction)

A user can move the sensor unit 1 to an optimal position for detecting a pulse wave by sliding the sensor unit 1 along sliding grooves. In this embodiment, a moving direction in which a position of a hard member such as the tendon 29 is avoided can be notified to a user in order to effect the movement correctly.

CPU 20 specifies as shown in the example processing 4 that a hard member such as the tendon 29 is located in a direction in which an inclination of a waveform of a DC component Pdc increases. CPU 20, when specifying a position of a hard member in such a way, selectively controls light-up of an LED in the LED section 10 based on the specified position of a hard member. Specification of a position of a hard member or specification of a position of the radial artery 27 may be performed according to any of the example processing 1 to 3. Description will be given of light-up control on an LED below with reference to FIGS. 16 to 18.

Figure 16:
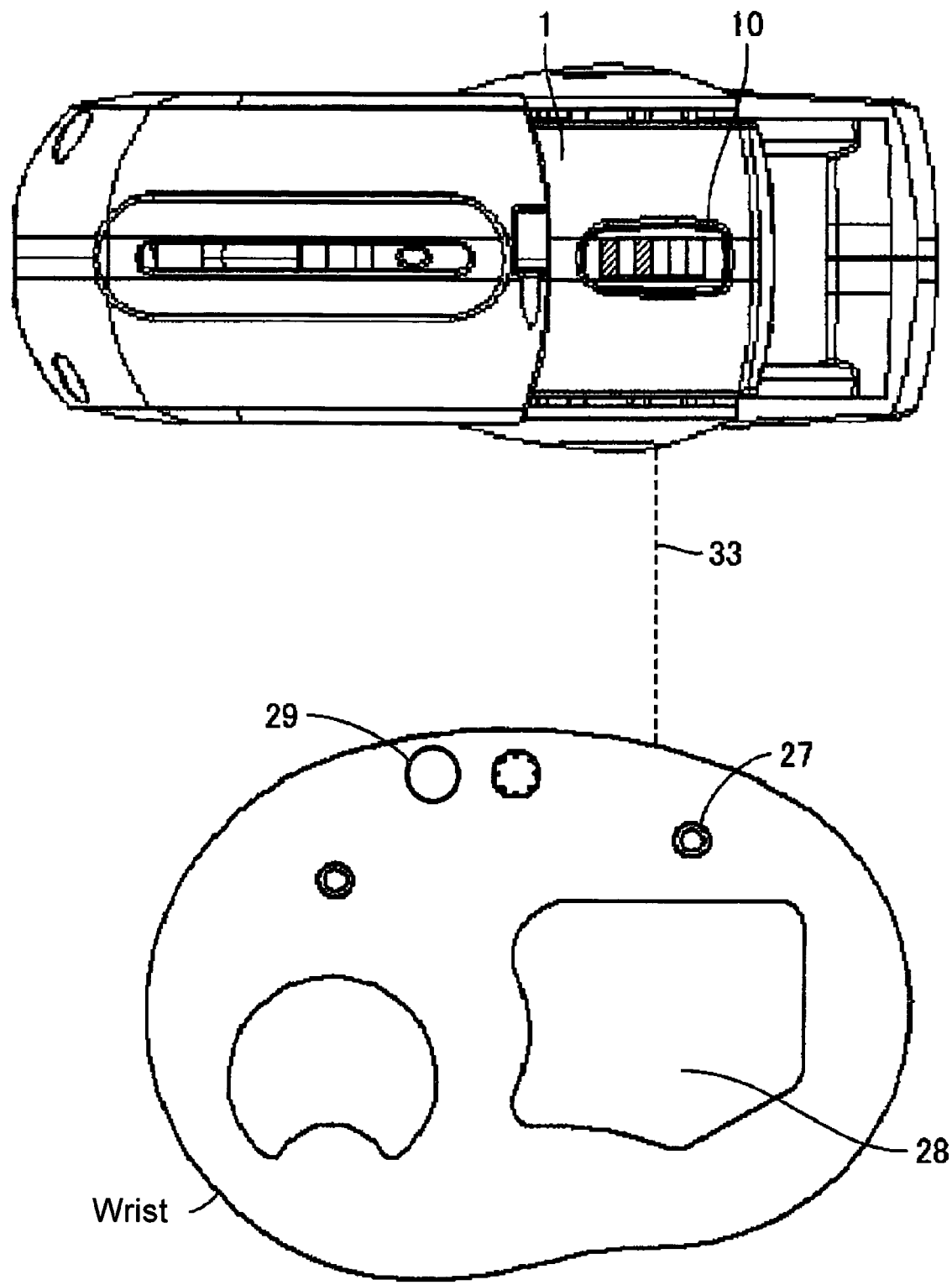
FIG. 16 shows views of a way notifying a position of a hard member relating to an embodiment of the invention.
Figure 17:
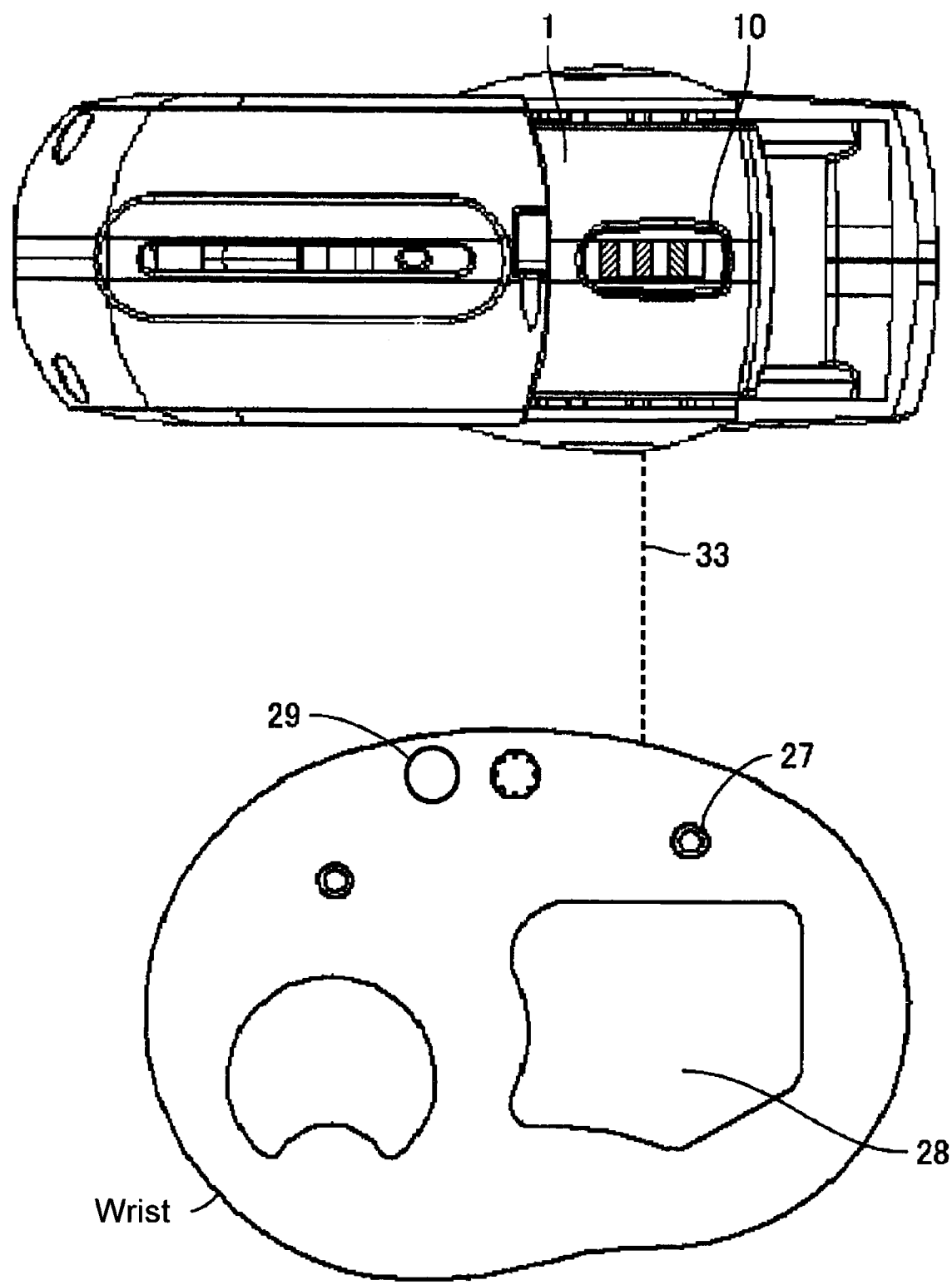
FIG. 17 shows views of a way notifying positions of a hard member and an artery relating to an embodiment of the invention.
Figure 18:
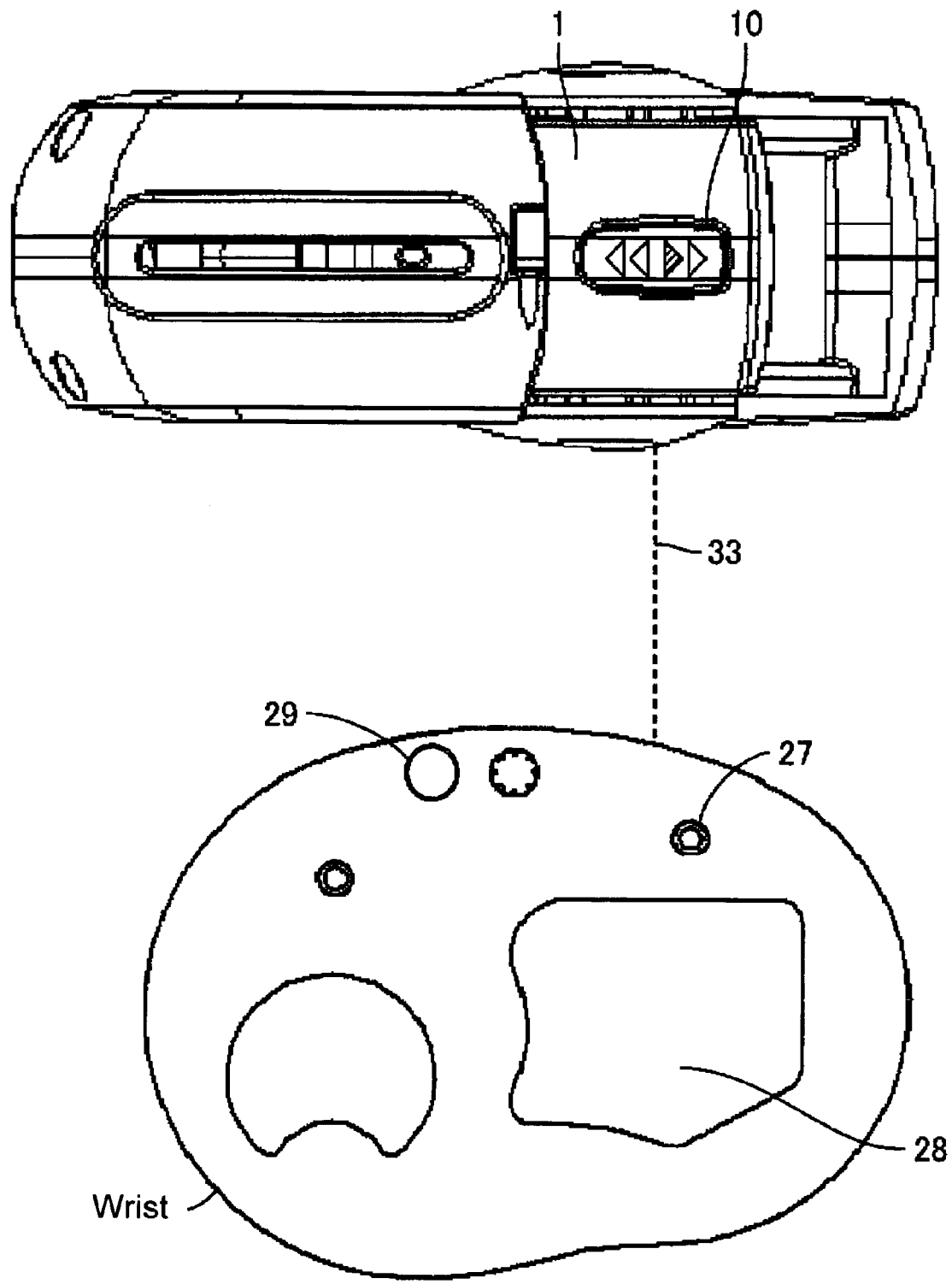
FIG. 18 shows views of a way notifying a direction in which a sensor unit is to be moved relating to an embodiment of the invention.

In FIGS. 16 to 18, a sectional view of a wrist and the sensor unit 1 mounted as in FIG. 5 on a surface of the wrist are shown being in position associated with each other relative to a center line 33 indicating the center of a pressure sensor array 11.

In FIG. 16, light-up is effected only on LEDs that are hatched, which are located in the left side of the center line 33 among plural LEDs in the LED section 10 disposed in parallel in a direction intersecting with the radial artery 27 of a wrist at an almost right angle. With the light-up of LEDs, a user can be notified that a hard member of the tendon 29 is located in the left side of the center of the pressure sensor array 11.

In FIG. 17, among plural LEDs in parallel disposed in the LED section 10, an LED that is hatched, which is located in the left side of the center line 33 is lighted up, for example, in green, while LEDs that are crosshatched, which are located in the right side of the center line 33 are lighted up, for example, in red, whereby a user can be notified that a hard member of the tendon 29 is located in the left side of the center of the pressure sensor array 11 and a candidate for the radial artery 27 is located in the right side thereof.

In FIG. 18, since a hard member of the tendon 29 is located in the left side of the center line 33 of the pressure sensor array 11 and a candidate for the radial artery 27 is located in the right side, it is notified with light-up of an LED or LEDs that the sensor unit 1 is recommended to be moved by sliding to a position slightly spaced from the current position to the right side thereof by lighting up an LED slightly spaced from the center line 33 to the right side thereof. LEDs of FIG. 18 indicates a direction with an arrow in order to point out a moving direction.

Note that while the notification is effected using the LED section 10, it may be done with the display unit 24 alone or a combination of the LED section 10 and the display unit 24.

The processing according to the flowchart of FIG. 6 starts when a start button not shown is turned on after the sensor unit 1 is moved by sliding following light-up of an LED as described above.

It should be understood that the embodiments disclosed above are presented by way of illustration but not by way of limitation in every respects. It is intended that the scope of the invention is not defined by the above description but by metes and bounds of the appended claims and includes all alterations and modifications of the embodiments without departing from the metes and bounds of the appended claims and the equivalence thereof.

According to the invention, pressure sensors other than the pressure sensor located above a hard member specified using information of a pressure component caused by the hard member among plural pressure sensors are selected as candidates for the pressure sensor located above an artery and a pulse wave generated in the artery is detected based on pressure information outputted by the selected pressure sensor. Accordingly, a pulse wave can be detected not at the position of the hard member differing from the artery but at the position of the artery.

What is claimed is:

1. A pulse wave detecting apparatus comprising:
a pressure sensor array that has a surface on which plural pressure sensors are disposed, the surface being pressed against an artery of a living human body so that a disposing direction of the pressure sensors intersects with the artery;
a pressurization section pressing the surface of the pressure sensor array against the artery;
a sensor selecting section selecting a candidate of the pressure sensor located above the artery from the pressure sensors in the pressure sensor array pressed by the pressurization section; and
a pulse wave detecting section detecting a pulse wave generated in the artery based on pressure information outputted from the pressure sensor selected by the sensor selecting section in the course where a pressurization force imposed on the pressure sensor array is continuously changed by the pressurization section, wherein
the sensor selecting section includes:
a pressure information acquiring section acquiring pressure information from the respective pressure sensors of the pressure sensor array simultaneously along the time axis; and
a hard member sensor excluding section extracting information on a pressure component caused by a hard member of the living human body different from the artery thereof, from the pressure information of the respective pressure sensors acquired by the pressure information acquiring section to specify the pressure sensor located above the hard member from the extracted pressure component information and to select the pressure sensors left after the specified pressure sensor is excluded from the plural pressure sensors as candidates of the pressure sensor located above the artery.

2. The pulse wave detecting apparatus according to claim 1, wherein the pressure information is a voltage signal, the pressure component information is the DC component of the voltage signal and
the hard member sensor excluding section extracts the DC component from the voltage signal to specify the pressure sensor located above the hard member based on a level of the extracted DC component.

3. The pulse wave detecting apparatus according to claim 2, wherein the hard member sensor excluding section specifies that the pressure sensor having a DC component at a level exceeding a predetermined level is a pressure sensor with a high possibility of being located above the hard member.

4. The pulse wave detecting apparatus according to claim 2, wherein the hard member sensor excluding section specifies that the pressure sensor with a DC component at the highest level among the plural pressure sensors is located above the hard member.

5. The pulse wave detecting apparatus according to claim 2, wherein the hard member sensor excluding section specifies the pressure sensor located above the hard member based on an inclination of a slope of a waveform obtained by connecting DC component levels of the plural pressure sensors in the disposing direction thereof.

6. The pulse wave detecting apparatus according to any one of claims 1 to 5, wherein the sensor selecting section further includes an artery position information generating section generating artery position information for selecting the pressure sensor located above the artery from pulse wave amplitude information and the pressure component information included in the pressure information of the respective pressure sensors acquired by the pressure information acquiring section.

7. The pulse wave detecting apparatus according to claim 6, wherein the pulse wave amplitude information is the AC component of a voltage signal, the AC component includes a pulse wave component and an artifact pulse wave and
the artery position information generating section includes an artifact removing section acquiring the pulse wave component left after the artifact pulse wave is removed from the AC component as the artery position information.

8. The pulse wave detecting apparatus according to claim 7, wherein the artifact removing section removes the artifact pulse wave from the AC component using the DC component.

9. The pulse wave detecting apparatus according to claim 8, wherein the artifact removing section removes the artifact pulse wave from the AC component by normalizing the AC component through division of the AC component by the DC component.

10. The pulse wave detecting apparatus according to claim 8, wherein the artifact removing section removes the artifact pulse wave from the AC component by subtracting the DC component from the AC component.

11. The pulse wave detecting apparatus according to any one of claims 1 to 5, further comprising a hard member position notifying section notifying the position of the hard member relative to the sensor array based on a position in the disposition of the pressure sensor specified as being located above the hard member by the hard member sensor excluding section.

12. The pulse wave detecting apparatus according to claim 11, wherein in the hard member position notifying section, notification is effected using light emitting units provided being related to the pressure sensor array.

13. The pulse wave detecting apparatus according to any one of claims 1 to 5, further comprising an artery position notifying section notifying a position of the artery relative to the pressure sensor array based on the position in the disposition of a candidate of the pressure sensor selected as being located above the artery by the sensor selecting section.

14. The pulse wave detecting apparatus according to claim 13, wherein in the artery position notifying section, notification is effected using light emitting units provided being related to the pressure sensor array.

15. The pulse wave detecting apparatus according to any one of claims 1 to 5, in which the pressure sensor array can be moved by sliding in the disposing direction thereof, further comprising a notification section notifying a sliding direction of the pressure sensor array for detecting a pule wave based on a position in the disposition of the pressure sensor specified as being located above the hard member by the hard member sensor excluding section.

16. The pulse wave detecting apparatus according to any one of claims 1 to 5, in which the pressure sensor array can be moved by sliding in the disposing direction thereof, further comprising a notification section notifying a sliding direction of the pressure sensor array for detecting a pulse wave based on a position in the disposition of a candidate of the pressure sensor selected as being located above the artery by the sensor selecting section.

17. The pulse wave detecting apparatus according to any one of claims 1 to 5, in which the pressure sensor array can be moved by sliding in the disposing direction thereof, further comprising a notification section notifying a sliding direction of the pressure sensor array for detecting a pulse wave based on a position in the disposition of the pressure sensor specified as being located above the hard member by the hard member sensor excluding section and a position in the disposition of a candidate of the pressure sensor selected as being located above the artery by the sensor selecting section.

18. The pulse wave detecting apparatus according to claim 17, wherein in the notification section, notification is effected using light emitting units provided being related to the pressure sensor array.

19. A method of detecting a pulse wave detecting a pulse wave generated in the artery of a living human body based on pressure information outputted from a pressure sensor in the course where a pressurization force imposed on a pressure sensor array, which has a surface on which plural pressure sensors are disposed, the surface being disposed above the artery of the living human body and being pressed against the artery thereof so that a disposing direction of the pressure sensors intersects with the artery, is continuously changed, comprising a sensor selecting step selecting a candidate of the pressure sensor located above the artery among the pressure sensors of the pressure sensor array, wherein the sensor selecting step includes:

a pressure information acquiring step of acquiring pressure information from the respective pressure sensors of the pressure sensor array simultaneously along the time axis; and a hard member sensor excluding step of extracting information on a pressure component caused by a hard member of the living human body different from the artery thereof from pressure information outputted by the respective pressure sensors acquired in the pressure information acquiring step to specify the pressure sensor located above the hard member from the extracted pressure component information and to select the pressure sensors left after the specified pressure sensor is excluded among the plural pressure sensors as candidates of the pressure sensor located above the artery.

* * * * *